United States Patent
Kim et al.

(10) Patent No.: US 11,730,084 B2
(45) Date of Patent: Aug. 22, 2023

(54) SYSTEM AND METHOD FOR AUTOMATICALLY GRIPPING AND CUTTING FRUITS AND PLANTS

(71) Applicant: Zordi, Inc., Boston, MA (US)

(72) Inventors: Hoon Ki Kim, Boston, MA (US); Matthew Luke Rockett, Jackson, TN (US); Casey Bennet Call, Franklin, TN (US); Youngsun Kim, Jackson, TN (US); Gilwoo Lee, Jackson, TN (US)

(73) Assignee: ZORDI, INC., Boston, MA (US)

( * ) Notice: Subject to any disclaimer, the term of this patent is extended or adjusted under 35 U.S.C. 154(b) by 0 days.

(21) Appl. No.: 17/728,915

(22) Filed: Apr. 25, 2022

(65) Prior Publication Data

US 2022/0346319 A1 Nov. 3, 2022

Related U.S. Application Data

(60) Provisional application No. 63/182,383, filed on Apr. 30, 2021.

(51) Int. Cl.
| | |
|---|---|
| *A01D 46/30* | (2006.01) |
| *B25J 11/00* | (2006.01) |
| *B25J 15/08* | (2006.01) |
| *A01D 75/00* | (2006.01) |
| *B25J 15/02* | (2006.01) |

(52) U.S. Cl.
CPC ............ *A01D 46/30* (2013.01); *A01D 75/00* (2013.01); *B25J 11/0055* (2013.01); *B25J 11/0085* (2013.01); *B25J 15/08* (2013.01); *B25J 15/02* (2013.01)

(58) Field of Classification Search
CPC .... A01D 75/00; A01D 46/30; B25J 15/00–12
See application file for complete search history.

(56) References Cited

U.S. PATENT DOCUMENTS

| | | | |
|---|---|---|---|
| 11,206,764 B1* | 12/2021 | Mazor | A01D 46/24 |
| 2012/0096823 A1* | 4/2012 | Moore | A01B 69/008 |
| | | | 56/153 |
| 2019/0261566 A1* | 8/2019 | Robertson | B25J 9/1697 |

(Continued)

FOREIGN PATENT DOCUMENTS

| | | | | |
|---|---|---|---|---|
| CN | 106863342 | * | 6/2017 | A01D 46/30 |
| CN | 106863342 A | * | 6/2017 | A01D 46/00 |

(Continued)

OTHER PUBLICATIONS

PCT International Search Report and Written Opinion, PCT Application No. PCT/US2022/026379, dated Aug. 26, 2022, 12 pages.

*Primary Examiner* — Adam J Behrens
(74) *Attorney, Agent, or Firm* — Fenwick & West LLP

(57) ABSTRACT

An autonomous robot for harvesting produce from a plant include a base, an arm coupled to the base, and an end-effector coupled to the arm. The end-effector includes one or more grippers, each having a first cutter, second cutter, and a compliant member between the first cutter and the second cutter. The first cutter is configured to cut a stem of the produce at a first location. The second cutter is configured to cut the stem of the produce at a second location. The compliant member is configured to plastically deform to hold the stem of the produce.

16 Claims, 20 Drawing Sheets

(56) References Cited

U.S. PATENT DOCUMENTS

2019/0381670 A1* 12/2019 Correll .................. B25J 9/1697
2020/0400518 A1* 12/2020 McKay ................. A01D 27/02
2021/0000013 A1    1/2021 Robertson et al.
2021/0368686 A1* 12/2021 Wisdom ................ B25J 9/0084

FOREIGN PATENT DOCUMENTS

| | | | | |
|---|---|---|---|---|
| CN | 107214716 A | * | 9/2017 | |
| CN | 108575320 A | * | 9/2018 | ............. A01D 46/30 |
| CN | 108582127 A | * | 9/2018 | ............. A01D 43/30 |
| CN | 108605510 A | | 10/2018 | |
| DE | 102020121554 A1 | * | 2/2022 | |
| EP | 1891852 A1 | * | 2/2008 | ............. A01D 46/30 |
| EP | 3539735 A1 | * | 9/2019 | ............. A01D 46/30 |
| JP | 2001095348 A | * | 4/2001 | |
| JP | 2011211969 A | | 10/2011 | |
| KR | 100784830 B1 | * | 12/2007 | |
| WO | WO-2016123656 A1 | * | 8/2016 | |
| WO | WO-2021144955 A1 | * | 7/2021 | |
| WO | WO-2022025758 A1 | * | 2/2022 | |

\* cited by examiner

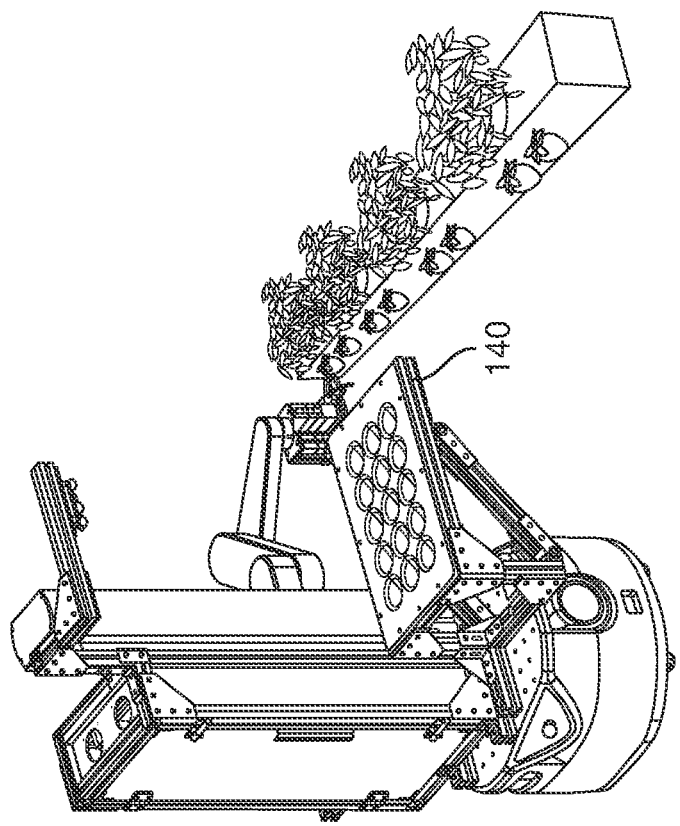
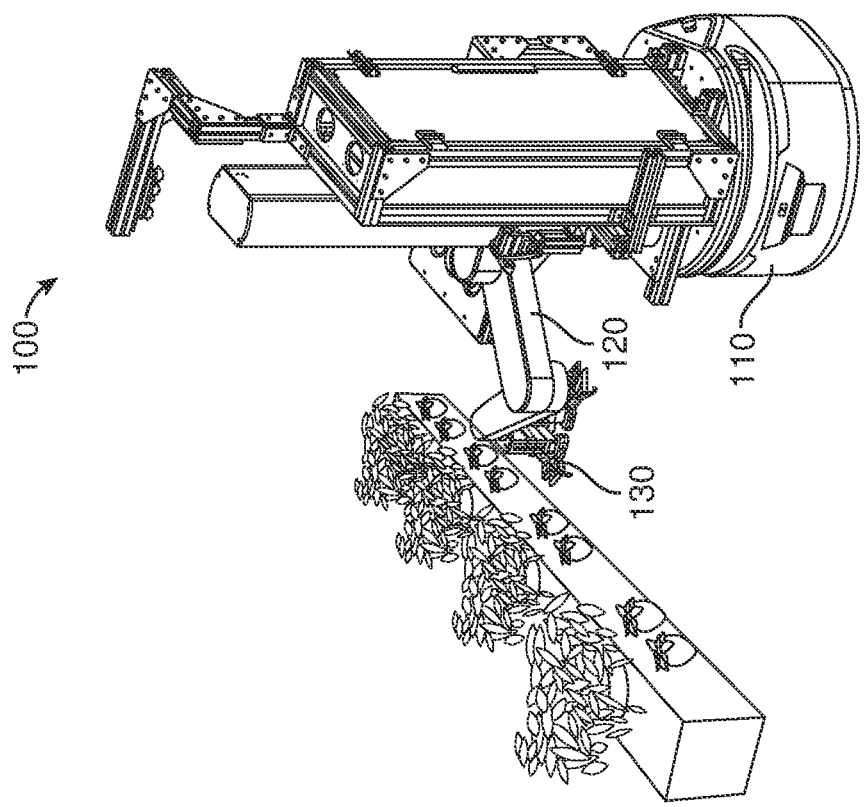
FIG. 1B
FIG. 1A

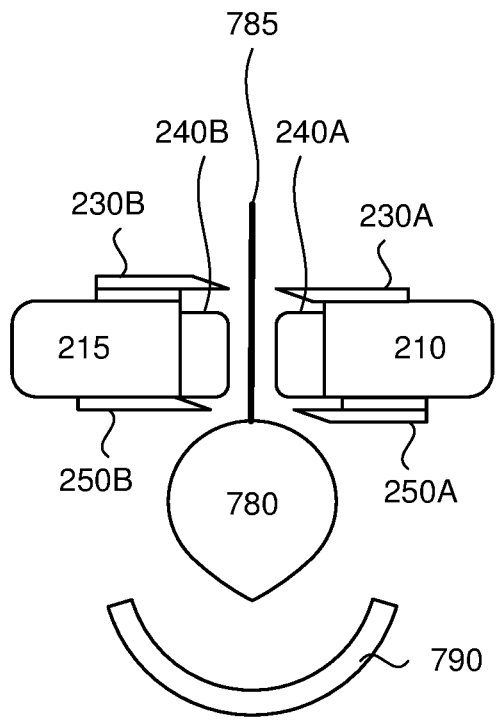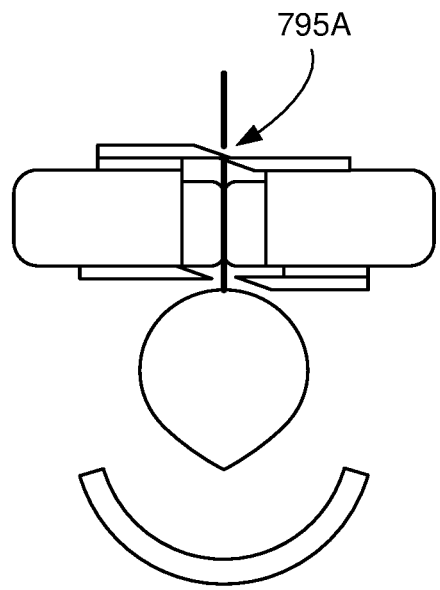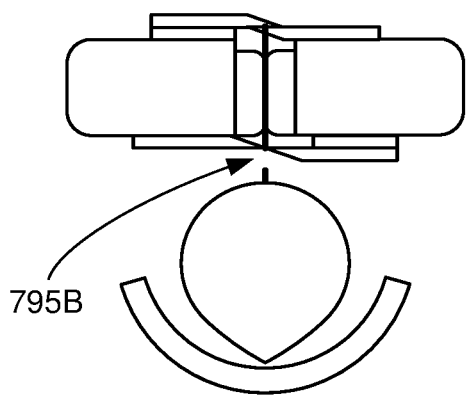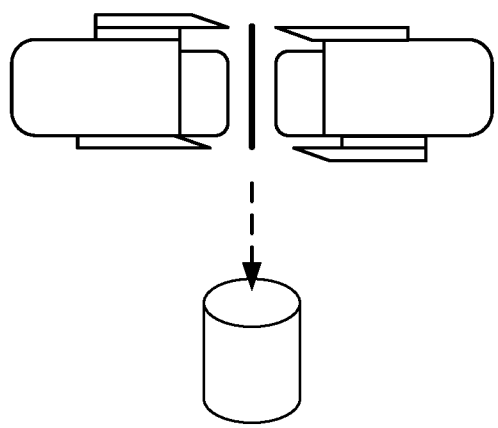
FIG. 7B
FIG. 7C
FIG. 7D
FIG. 7E

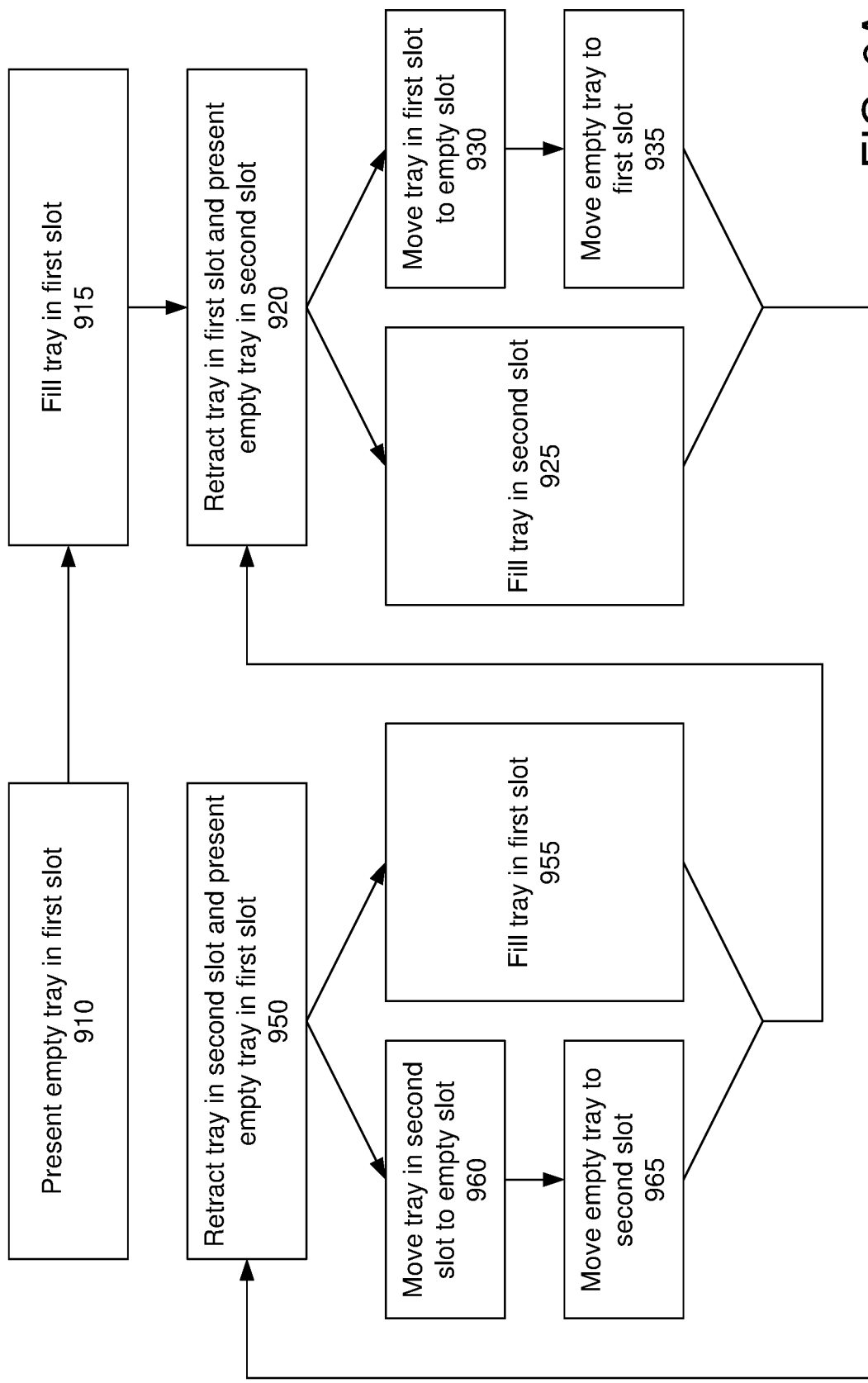

SYSTEM AND METHOD FOR AUTOMATICALLY GRIPPING AND CUTTING FRUITS AND PLANTS

CROSS REFERENCE TO RELATED APPLICATIONS

This application claims the benefit of U.S. Provisional Patent Application No. 63/182,383, filed on Apr. 30, 2021, which is incorporated by reference in its entirety.

BACKGROUND

1. Field of Art

The disclosure generally relates to the field of robotics, and more specifically to an automated produce harvesting robot.

2. Description of the Related Art

Harvesting produce (such as fruits or vegetables) can be labor intensive. Each fruit or vegetable may need to be individually detached from a plant. However, the fruits or vegetables may be fragile and may be prone to being damaged as they are detached from the plant. For example, strawberries have a soft flesh that can be crushed if too much force is applied to the fruit while the fruit is being picked. Damaged fruits or vegetables decrease the desirability of the fruit or vegetable, ultimately reducing the value of the fruit or vegetable. In addition, during harvesting, it is desirable to reduce the amount of contact with the fruit or vegetable being harvested due to food safety reasons. For example, by handing fruits or vegetables being harvested, the likelihood of transferring mold or bacteria present in one fruit or vegetable to another is increases. As such, there is a need for an automated tool that can gently remove fruits or vegetables from plants and gently place them into trays or packages in a manner that reduces the risk of damaging the fruits or vegetables and in a manner that reduces the amount of handling of the fruit or vegetable being harvested.

SUMMARY

An autonomous robot for harvesting plant material (e.g., fruits, vegetables, flowers, leaves, etc.) from a plant include a base, an arm coupled to the base, and an end-effector coupled to the arm. The end-effector includes one or more grippers, each having a first cutter, second cutter, and a compliant member between the first cutter and the second cutter. The first cutter is configured to cut a stem of the plant material at a first location. The second cutter is configured to cut the stem of the plant material at a second location. The compliant member is configured to plastically deform to hold the stem of the plant material. As such, the autonomous robot is configured to handle the plant material by holding the plant material by its stem, thus reducing the amount of contact between the autonomous robot and the plant material being harvested.

In some embodiments, the autonomous robot additionally includes a disinfecting module for disinfecting the components of the end-effector (such as the first cutter, the second cutter, and the compliant member), and for disinfecting the plant material being harvested. The disinfecting module includes one or more tubes configured to deliver one or more chemicals, one or more nozzles for spraying the one or more chemicals, and a chemical distributer coupled between the one or more tubes and the one or more nozzles. The chemical distributer is configured to control a flow of the one or more chemicals from the one or more tubes to the one or more nozzles.

In some embodiments, the autonomous robot additionally includes one or more collection trays for collecting the plant material harvested from the plant. In addition, the autonomous robot may include a tray cycler configured to hold the one or more collection trays. The tray cycler may be configured to retract a first collection tray arranged in a first slot of the tray cycler and present a second collection tray arranged in a second slot of the tray cycler in response to the first tray being full. Moreover, as the autonomous robot fills the second tray, the tray cycler is configured to move the first collection tray from the first slot of the tray cycler to a third slot of the tray cycler and to move a third collection tray from a fourth slot of the tray cycler to the first slot of the tray cycler. Thus, when the second tray fills up, the tray cycler is able to present the third collection tray to enable the autonomous robot to keep harvesting the plant material.

In some embodiments, the autonomous robot further includes a pitch axis actuator for attaching the end-effector to the arm. The pitch axis actuator is configured to rotate an angle of the end-effector with respect to the arm. Moreover, the pitch axis actuator is configured to tilt the end-effector while the end-effector is holding the stem of the plant material to align a side surface of the plant material to a bottom surface of a collection slot for collecting the plant material and reduces the risk of the plant material being damaged during the placement or transportation, which is especially critical for soft fruits.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 1A and FIG. 1B illustrate perspective views of an autonomous robot for harvesting produce, according to one or more embodiments.

FIGS. 7B through 7E illustrate front views of the gripper at various stages in the process for harvesting produce of FIG. 7A.

FIG. 9A illustrates a flow diagram of a process for cycling through collection trays, according to one or more embodiments.

DETAILED DESCRIPTION

Figure 1D:
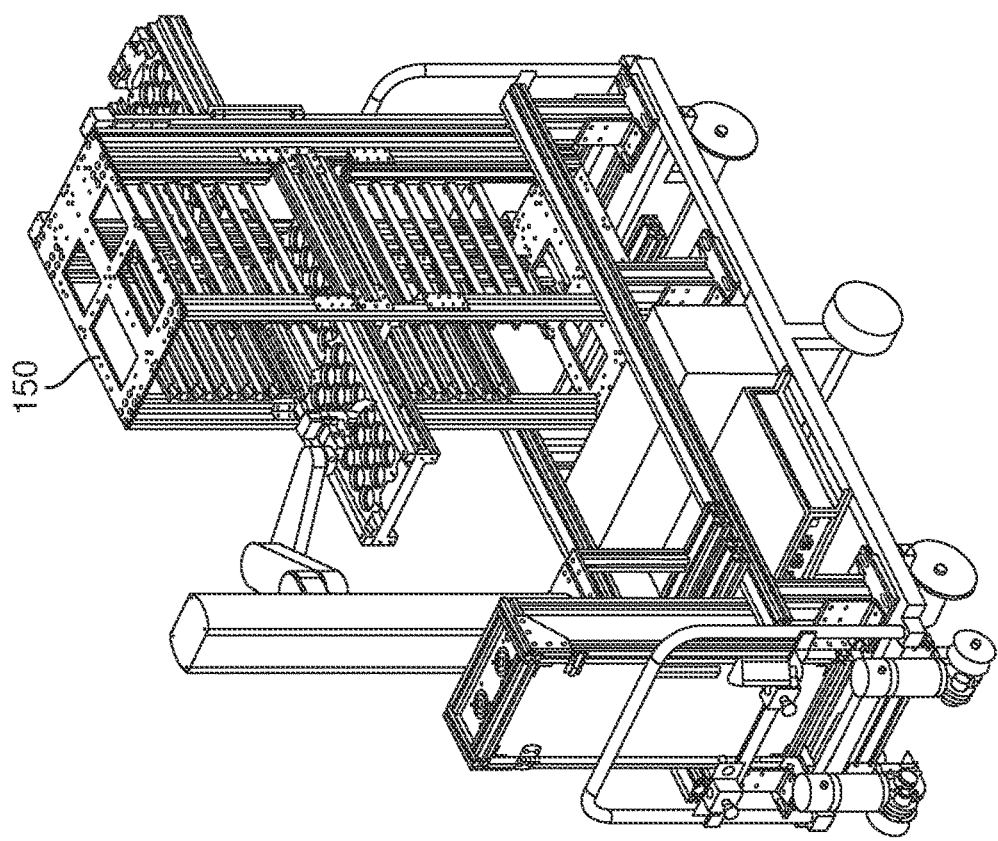
FIG. 1C and FIG. 1D illustrate perspective views of an autonomous robot for harvesting produce and having an automated collection tray cycler, according to one or more embodiments.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Disclosed herein is an automated harvester of fruits and/or pruning of plants. FIG. 1A and FIG. 1B illustrate perspective views of an autonomous harvesting robot for harvesting produce, according to one or more embodiments. The harvesting robot 100 includes a base 110, one or more arms 120, one or more end-effectors 130, and one or more collection trays 140. In some embodiments, the harvesting robot 100 includes additional components such as electronics and sensors that are not shown in FIGS. 1A and 1B.

The base 110 may include rollers or wheels for allowing the harvesting robot to move around a field or greenhouse. In some embodiments, the harvesting robot may include sensors and controllers for controlling the movement of the harvesting robot around the field or greenhouse. The base 110 may include attachment points or structures for allowing various attachments (such as one or more arms, one or more collection trays, battery packs, etc.) to be attached to the harvesting robot.

The arm 120 is coupled to the base 110 and is configured to position the end-effector 130 near an item to be picked or cut. Moreover, the arm 120 is configured to translate a picked item to a collection tray 140. The arm 120 may allow the end-effector 130 to be moved vertically, laterally, and to rotate the end-effector about one or more axis of rotation. In some embodiments, the harvesting robot 100 includes multiple arms, each coupled to a corresponding end-effector.

The one or more end-effectors 130 enable efficient harvesting of various items (e.g., as produce like fruits or vegetables) and/or for pruning various plant parts. Examples of the uses of the end-effectors 130 include farming and gardening. Each end-effector 130 includes one or more grippers having a set of cutters or cutting elements for detaching fruits or vegetables from the plants. The end-effector may include a set of sensors and cameras for controlling the operation of the one or more grippers. The sensors of the end-effectors may be attached or mounted directly on the end-effector, or may be placed elsewhere (such as the arm or base of the harvesting robot) to facilitate automation of the end-effector or other components of the harvesting robot. A more detailed description of the end-effector 130 and the grippers of the end-effector is provided hereinbelow in conjunction with FIGS. 2A-2D, 3A-3C, and 4A-4B.

The collection trays 140 are configured to hold items harvested by the harvesting robot 100. The collection trays 140 include a set of slots, each configured to hold one or more harvested items. In some embodiments, the harvesting robot may be equipped with collection trays having slots with different dimensions based on the type of item being harvested. For example, the harvesting robots may be equipped with collection trays having small slots when harvesting small fruits and equipped with collection trays having larger slots when harvesting large vegetables. In some embodiments, the collection trays are instead configured to hold one or more consumer packages (such as plastic or cardboard boxes) for packaging the items being harvested. As such, the harvesting robot 100 may be able to directly place the items being harvested into the end consumer packages to be sold consumers.

Figure 1C:
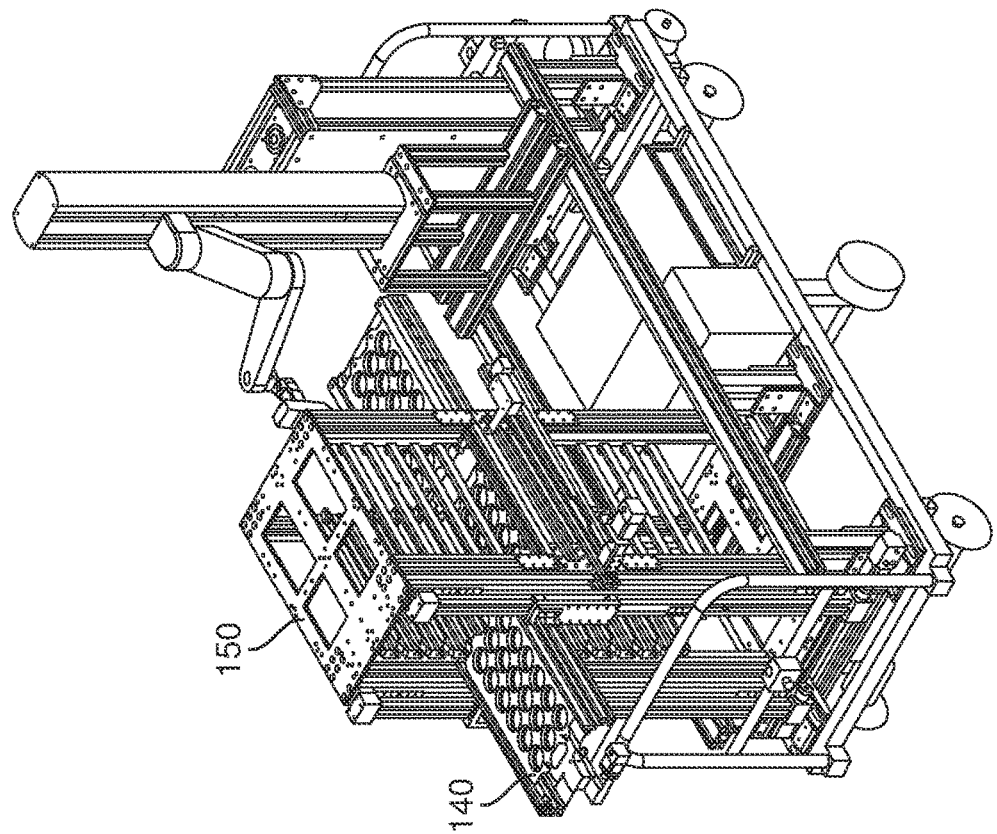

FIG. 1C and FIG. 1D illustrate perspective views of an autonomous robot for harvesting produce and having an automated collection tray cycler 150, according to one or more embodiments. The collection tray cycler 150 is configured to hold multiple collection trays 140. In some embodiments, the collection tray cycler 150 is configured to dispense a collection tray to a collection area to enable the harvesting robot to place harvested items into the slots of the collection tray. The collection tray cycler 150 may include a mechanism to rotate through the set of collection trays 140. That is, as a collection tray fills up, the collection tray cycler 150 replaces the filled collection tray with empty collection trays. The collection try cycler 150 may be configured to dispense the collection trays in a location that reduces the amount of time for moving the end-effector from a location where the item was located when harvested to the location where the collection tray is located. For example, the collection tray cycler may dispense the collection trays at a height that is based on the location of the fruits or vegetable being harvested from a plant.

Figure 2A:
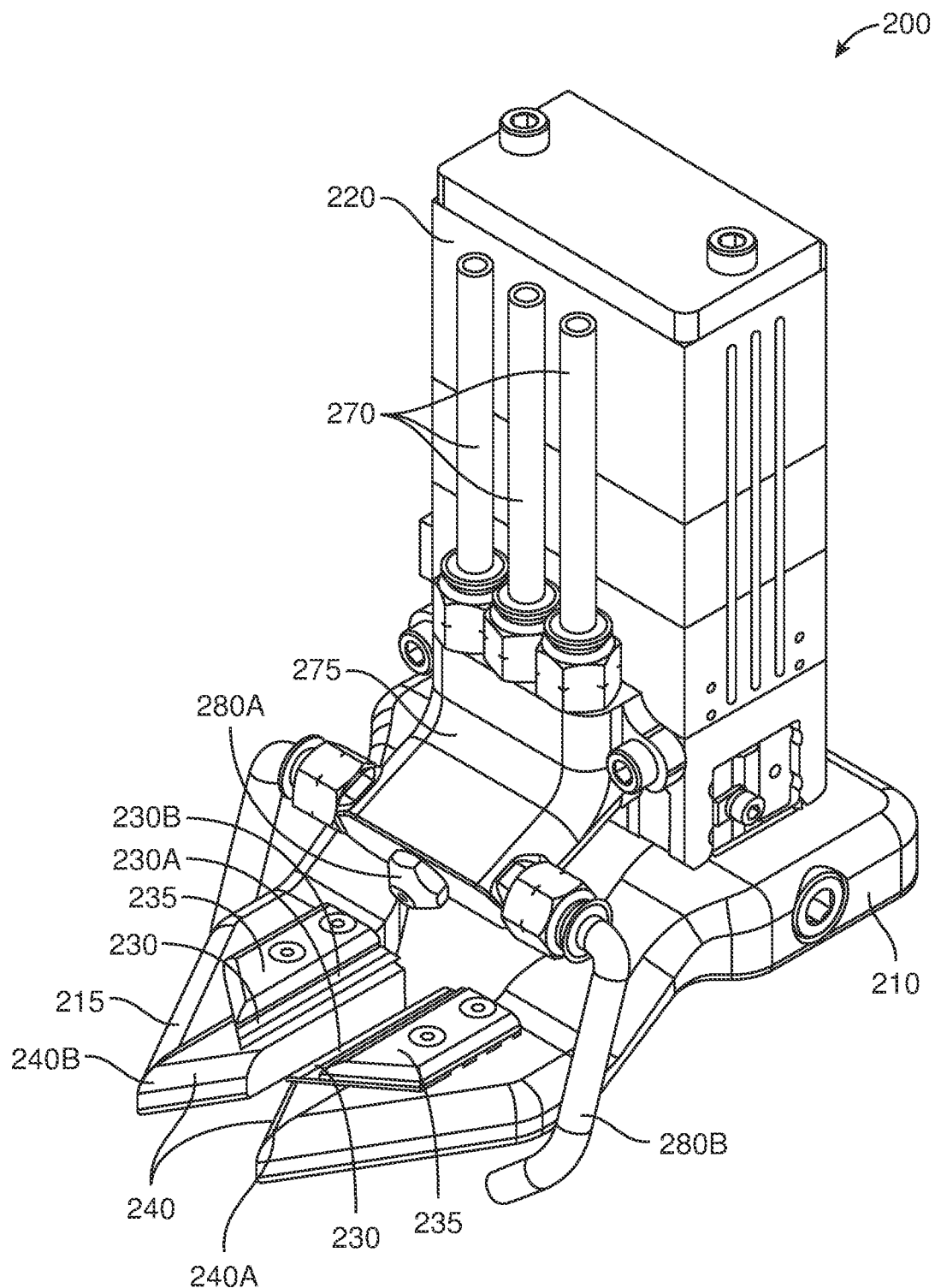
FIG. 2A illustrates a perspective view of an end-effector 130 for harvesting produce, according to one or more embodiments.
Figure 2B:
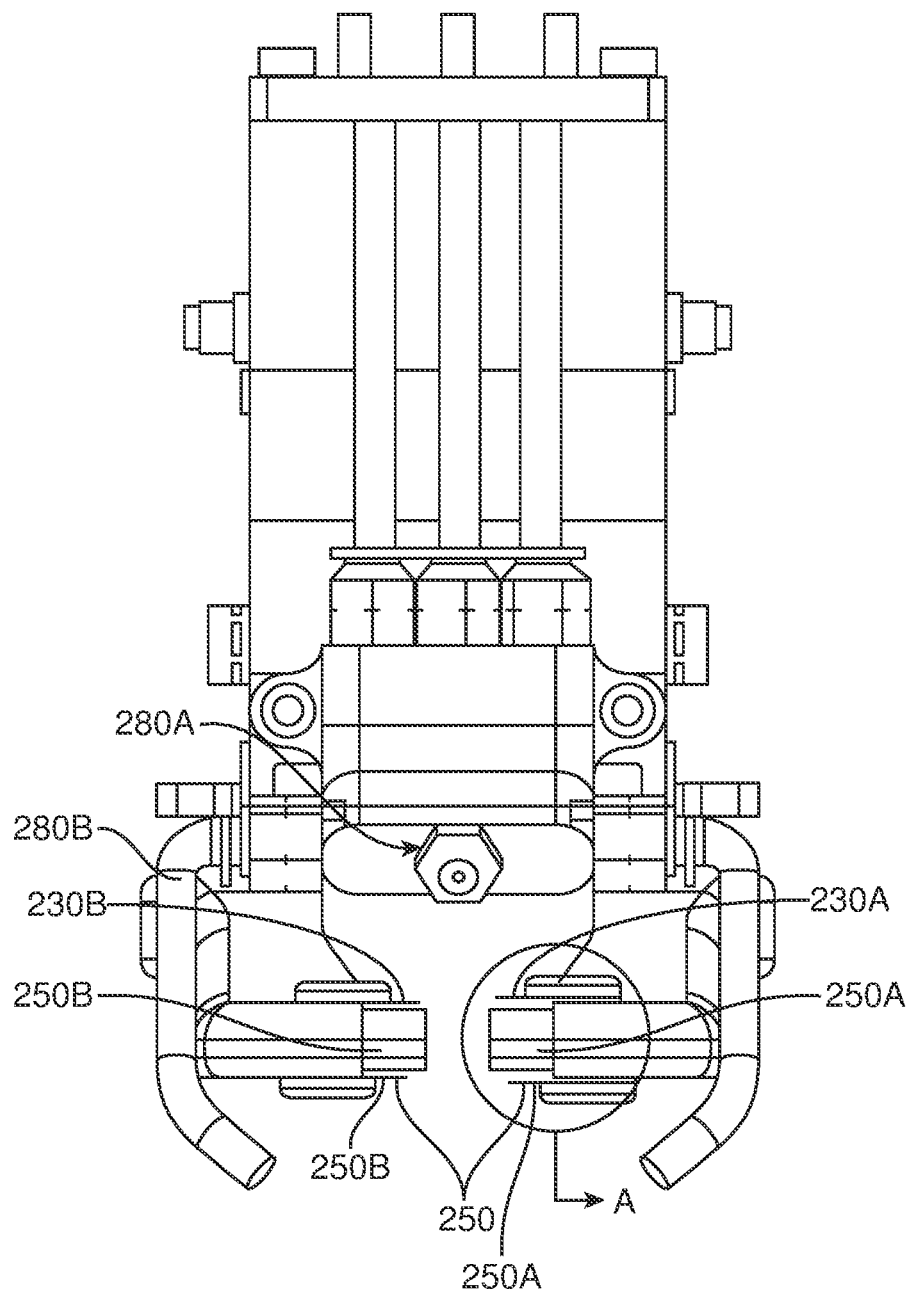
FIG. 2B illustrates a front view of an end-effector, according to one or more embodiments.
Figure 2C:
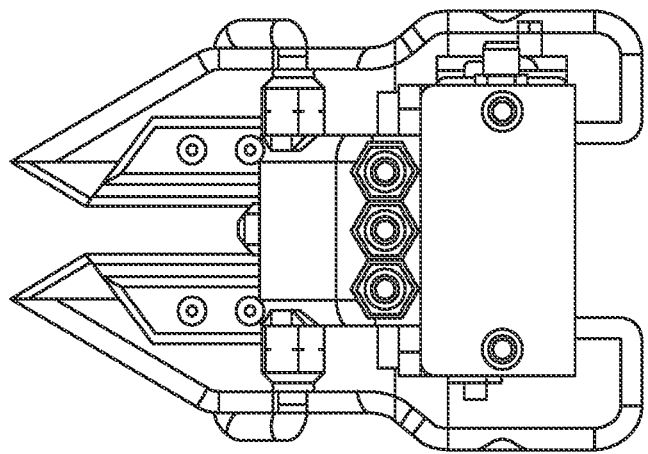
FIG. 2C illustrates a top view of an end-effector, according to one or more embodiments.
Figure 2D:
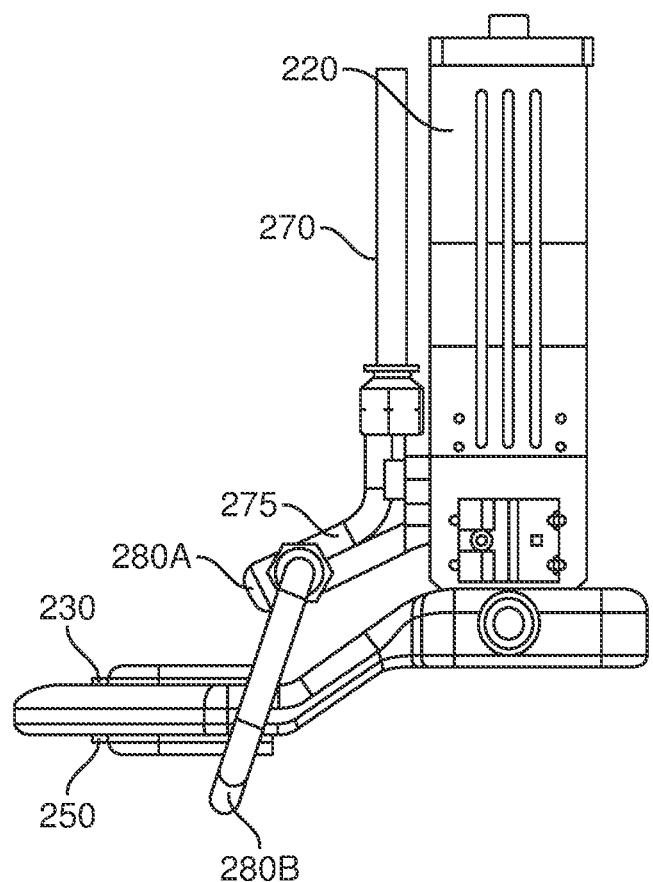
FIG. 2D illustrates a side view of an end-effector, according to one or more embodiments.

FIG. 2A illustrates a perspective view of an end-effector 130 for harvesting produce, according to one or more embodiments. FIG. 2B illustrates a front view of an end-effector, according to one or more embodiments. FIG. 2C illustrates a top view of an end-effector, according to one or more embodiments. FIG. 2D illustrates a side view of an end-effector, according to one or more embodiments.

The end-effector 130 includes one or more grippers 200 configured to cut stems of a plant for harvesting a fruit attached to an end of the stem, and for transferring the fruit to a collection tray. The gripper 200 includes an upper cutting element, a holding member, a lower cutting element, an actuator, and a disinfecting module. In some embodiments, the upper cutting element, the holding member, and the lower cutting element are disposed on a pair of gripper fingers that can be opened or closed by the actuator.

Figure 3A:
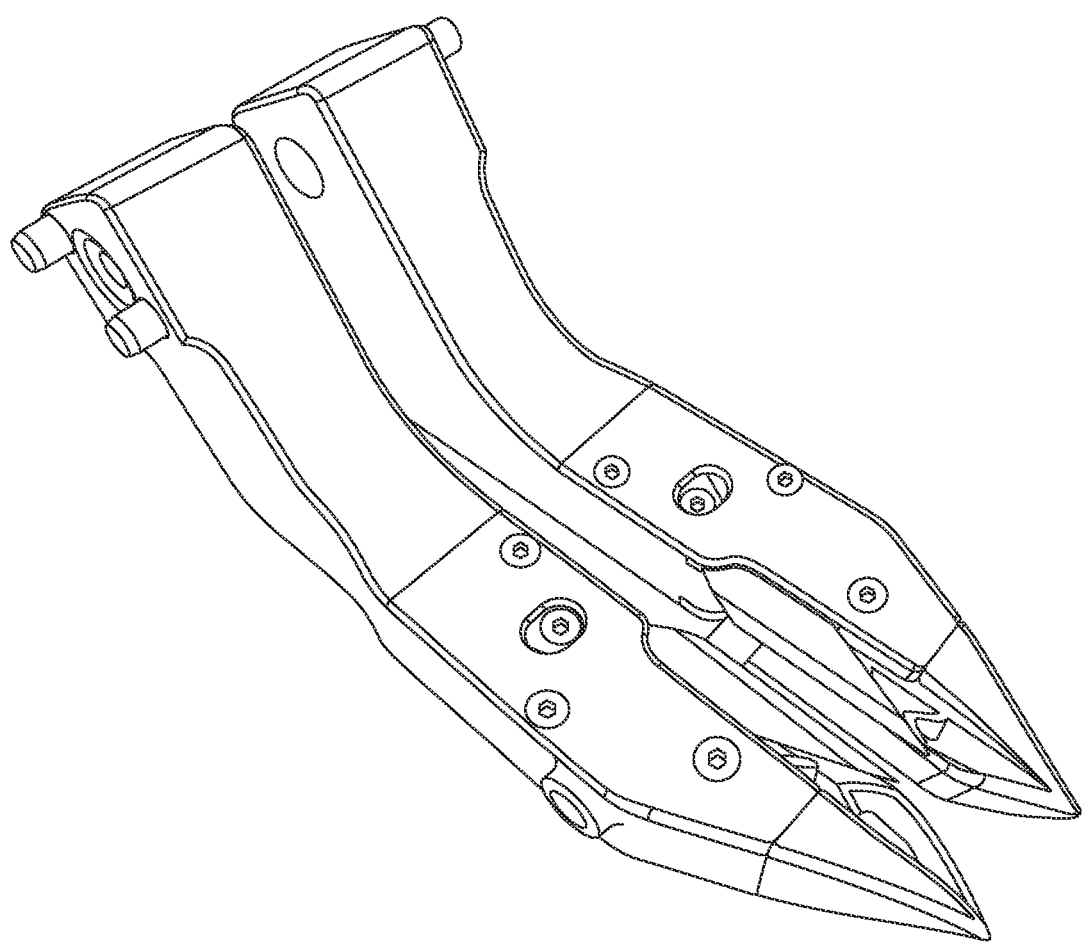
FIG. 3A illustrates a perspective view of a pair of gripper fingers, according to one or more embodiments.
Figure 3C:
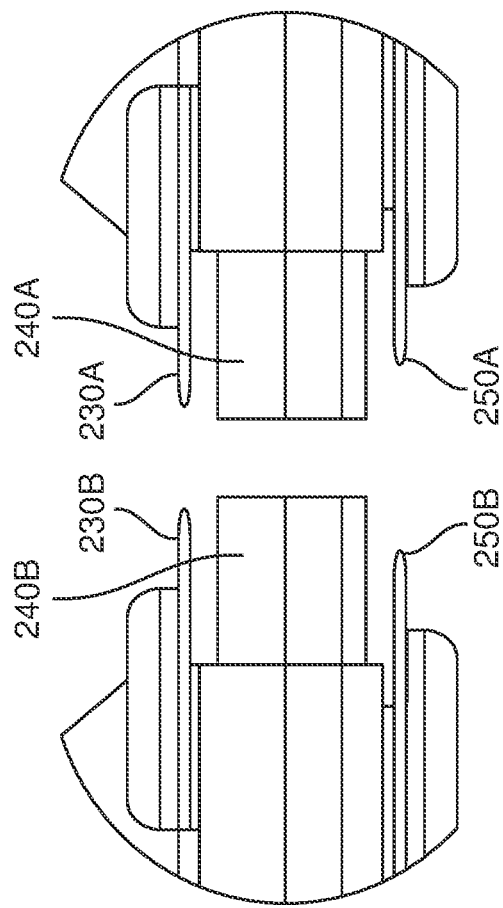
FIG. 3C illustrates a front view of the tip of a gripper finger, according to one or more embodiments.
Figure 3B:
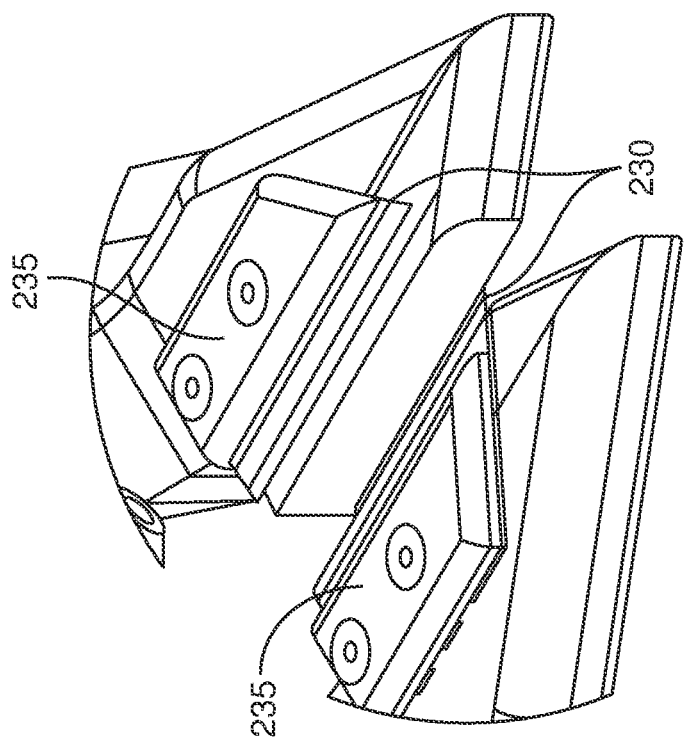
FIG. 3B illustrates a zoomed in perspective view of the tip of a pair of gripper fingers, according to one or more embodiments.

FIG. 3A illustrates a perspective view of a pair of gripper fingers, according to one or more embodiments. FIG. 3B illustrates a zoomed in perspective view of the tip of a pair of gripper fingers, according to one or more embodiments. FIG. 3C illustrates a front view of the tip of a gripper finger, according to one or more embodiments.

Referring back to FIGS. 2A-2D and 3A-3C together, the pair of gripper fingers may include a left gripper finger 210 and a right gripper finger 215. At least one of the left gripper finger 210 and the right gripper finger 215 are coupled to the actuator 220. The actuator 220 is then configured to laterally move at least one of the left gripper finger 210 and the right gripper finger 215 to open or close a gap between the left gripper finger 210 and the right gripper finger 215. In some embodiments, both the left gripper finger 210 and the right gripper finger 215 are coupled to the actuator 220. The actuator 220 is then configured to move the left gripper finger 210 and the right gripper finger 215 in opposite directions to open or close the gap between the left gripper finger and the right gripper finger.

The gripper fingers 210 and 215 may have a sharp tip to help the gripper 200 to move through gaps between stems of a plant to position the gripper 200 at a position for removing a fruit or a vegetable from the plant. In some embodiments, the gripper fingers 210 and 215 are bent or angled to enable easier and safer placement of the gripper around a stem for harvesting a fruit or vegetable, and for easier and safer positioning of the gripper above a collecting tray for collecting the fruit or vegetables. The gripper fingers 210 and 215 may be made of chemical resistant and rust-free materials such as anodized aluminum or stainless steel.

The upper cutting element (e.g., first cutter) is configured to cut a stem at a first location. The upper cutting element is further configured to detach plant parts (e.g., fruits, vegetables, flowers, long stems, leaves, etc.) from the plant by cutting the stem at the first location. The upper cutting element may include a pair of blades 230. The pair of blades of the upper cutting element includes a left upper blade 230A attached to the left gripper finger 210 and a right upper blade 230B attached to the right gripper finger 215. The blades 230 of the upper cutting element may be made of chemical resistant and rust-free materials such as anodized aluminum or stainless steel. The left upper blade 230A and the right upper blade 230B may be attached to an upper surface of the left and right gripper fingers respectively. In some embodiments, the blades 230 of the upper cutting element are held in place by blade clamps 235. The blade clamp 235 may be used in order to keep the blades 230 flat on their respective gripper fingers. The blade clamps may be able to be disassembled to allow for replacement of the blades 230. The blade clamps 235 may be made of a chemical resistant and rust free (or rust resistant) material (such as certain metals or plastics) to reduce the likelihood of contamination of the harvested fruit or vegetable and the plant.

The upper cutting element (including the left upper blade 230A and the right upper blade 230B) is configured to close and cut objects that are placed between the blades 230 of the upper cutting element when the left gripper finger 210 and the right gripper finger 215 are actuated to be at a first position. As the left gripper finger 210 and the right gripper finger 215 are actuated to close from an open position to the first position, a gap between the blades 230 of the upper cutting element is closed, causing an object placed in the gap between the blades 230 of the upper cutting element to be cut.

In some embodiments, after each cutting operation, the blades 230 of the upper cutting element may be cleaned to avoid contaminating the plant during the next cutting operation. Moreover, after a number of operations, the blades 230 of the upper cutting element can be replaced to keep the blades sharp.

The holding member is configured to grab an object that was cut by the upper cutting element. For instance, the holding member is configured to grab onto a length of stem that is attached to a fruit or vegetable after the stem was cut by the upper cutting element to remove the fruit or vegetable from a plant. By holding the fruit or vegetable by the stem, the gripper is able to harvest and store the fruit or vegetable without touching the actual fruit or vegetable itself. This helps to achieve an increased quality of the produce item being harvested by the gripper 200.

The holding member may include a pair of compliant elements 240. The pair of compliant elements are configured to plastically deform to exert a force to an object that is placed between the pair of compliant elements. The pair of compliant elements may be able to conform to the shape of the object to allow the holding member to firmly grab the object. The pair of compliant elements 240 include a left compliant element 240A attached to the left gripper finger 210 and a right compliant element 240B attached to the right gripper finger 215. As the left gripper finger 210 and the right gripper finger 215 are actuated to close, the gap between the left compliant element 240A and the right compliant element 240B closes, causing the left compliant element 240A and the right compliant element 240B to press on the object placed in the gap between the left compliant element 240A and the right compliant element 240B. The pressure applied by the left compliant element 240A and the right compliant element 240B results in frictional forces to be applied to the surface of the object placed in the gap between the left compliant element 240A and the right compliant element 240B.

In some embodiments, the compliant element 240 is made of a food safe and chemical resistant material to keep the fruit or vegetable from being contaminated. The compliant elements 240 may be made of a foam or plastic material that are able to plastically deform when force is applied to the side surfaces of the compliant elements 240, and to return to an original shape when the force is removed.

The lower cutting element (e.g., second cutter) is configured to cut a stem at a second location. In one embodiment, the second position is closer to the fruit to be cut than the first position. The lower cutting element is further configured to release the harvested fruit or vegetable by cutting an excess length of the stem that was used by the gripper 200 to grab onto to harvested fruit or vegetable. The lower cutting element may be configured to cut the stem at a location below the first location where the upper cutting element is configured to cut the stem. The lower cutting element may include a pair of blades 250 (FIG. 2B). The pair of blades of the lower cutting element includes a left lower blade 250A attached to the left gripper finger 210 and a right lower blade 250B attached to the right gripper finger 215. The left lower blade 250A and the right lower blade 250B may be attached to a bottom surface of the left and right gripper fingers respectively. In some embodiments the blades 250 of the lower cutting element are held in place by blade clamps 235.

The lower cutting element is configured to close to cut objects that are placed between the blades 250 of the lower cutting element when the left gripper finger 210 and the right gripper finger 215 are actuated to be in a second position. In some embodiments, the blades 250 of the lower cutting elements are separated by a gap wider than the gap of the blades 230 of the upper cutting element. As such, when the left gripper finger 210 and the right gripper finger 215 are actuated to close to the first position, the upper cutting element is able to cut the object places between the left gripper finger 210 and the right gripper finger 215, but the lower cutting element is not yet able to cut the object. In order for the lower cutting element to cut the object, the left gripper finger 210 and the right gripper finger 215 are actuated to close to the second position.

In various embodiments, the upper cutting element or the lower cutting element can be oriented in a variety of different ways such as in parallel or angular with single or double blades. For a parallel blade orientation, a back-end stopper (not shown) may be attached between the left and right fingers, connecting the left and right fingers where the blades start (e.g., close to the actuator 220). As the gripper approaches a stem and the stem gets between the two blades, the back-end stopper prevents the stem from getting too far inside and missing the blades entirely. The back-end stopper compensates for inaccuracy of the target position depending on the fruit or vegetable which is the target of harvesting.

The actuator 220 may be actuated using fluid or electric power source with sensing and controlling capabilities of position, velocity, and force of the fingers. A force and speed of the actuator 220 for moving the gripper fingers 210 and 215 may vary depending on the size and physical strength of a target fruit or vegetable. The outer-most surface of the actuator 220 may be made of chemical resistant and rust-free material such as anodized aluminum or stainless steel. Alternatively, or in addition, a cover is be mounted to protect the surfaces of the actuator 220. The actuator 220 may be mounted at different joint of angles depending on the shape and the structure of the target plant.

The disinfecting module is configured to dispense a disinfecting solution disinfect at least a portion of the gripper. For example, the disinfecting module is configured to dispense the disinfecting solution to disinfect the upper cutting element and or the lower cutting element of the gripper. In some embodiments, the disinfecting module is configured to disinfect the gripper each time the gripper is used for harvesting a fruit or vegetable. This prevents cross-contamination between fruits or vegetables, and prevents transmission of diseases to the plants.

In some embodiments, the disinfecting module is additionally configured to clean or disinfect the fruits or vegetables picked by the gripper. The disinfecting module may dispense a cleaning or disinfecting solution to the fruit or vegetable (e.g., after the fruit or vegetable is harvested from the plant by cutting a stem of the fruit or vegetable using the upper cutting element, and while the holding member is holding the fruit or vegetable). The disinfecting and/or cleaning of the fruit or vegetable may improve the lifetime of the fruit or vegetable.

The disinfecting module may be capable of applying chemicals in liquid and/or gas form. The type of chemical may range from a typical wax coating material to a noble gas such as Argon gas which help with the shelf life.

In some embodiments, the direction of the nozzles of the disinfecting module may be manipulated (e.g., using the robot's arm) to apply chemicals to the live plant as well. Chemicals such as ethylene gas may be applied to fruits on the plant to age the fruits and accelerate the growth rate. Nutrient for foliar fertilizer applications such as nitrogen, potassium, and calcium may also be applied to the plant. To help keep plants healthy while reducing the chance of the plants encountering fungi, weeds, and/or insects, different types of preventive and curative products such as fungicides, herbicides, and insecticides may also be applied.

The disinfecting module may include a set of tubes 270, a chemical distributer 275, and one or more nozzles 280. The tubes 270 are configured to deliver one or more chemical (such as cleaning or disinfecting fluids) to the chemical distributer 275. The tubes 270 may be made of a chemical resistant material to prevent the tubes from being damaged. The tubes 270 may be made of a flexible material to confirm the tubes' shape to various motions of the robot 100. In some embodiments, the tubes 270 are connected to containers holding the various chemicals used for cleaning or disinfecting the gripper and/or the fruits or vegetables. Moreover, the tubes 270 may be connected to pumps for pumping the various chemicals used for cleaning or disinfecting the gripper and/or the fruits or vegetables.

The chemical distributer 275 is configured to control the flow of the different chemicals received through the tubes 270 to the nozzles 280. The chemical distributer 275 may include nozzles, tube fittings, valves, and the like. In some embodiments, the chemical distributer 275 includes actuators for mixing chemicals. For example, the chemical distributer 275 may mix two or more chemicals at a predetermined ratio prior to allowing the mixture to flow through the nozzles 280.

The set of nozzles 280 are configured to spray chemicals delivered by the chemical distributer 275. The nozzles 280 may be made of corrosion resistant and chemical resistant material such as nickel-plated brass or stainless steel. The set of nozzles may include a blade misting nozzle 280A and one or more plant misting nozzle 280B. The blade misting nozzle 280A is configured to apply different types of chemicals to clean and disinfect the blades 230 of the upper cutting element and/or the blades 250 of the lower cutting element. The plant misting nozzle 280B is configured to apply a coating or supplementary chemical directly onto the harvested fruit or vegetable to enhance the quality of the produce, or onto pruned plant parts for disinfection and pest/disease management.

Some or all components of the gripper may be made of chemical resistant and rust-free materials such as anodized aluminum or stainless steel. The components that physically touch the fruit/vegetable and/or stem of the fruit/vegetable such as the blades of the upper cutting element, the holding member, and the blades of the lower cutting element may be made from food-safe material which can be disinfected after use and/or at other suitable times and can easily be replaced.

The above described functionality of gripper can be used for pruning operation as well. The end-effector may be attached at a different angle to better serve pruning purposes or harvesting purposes. The gripper operation is controlled by software that can be executed by a processor on the robot, on the harvester, or is located remotely.

Figure 3E:
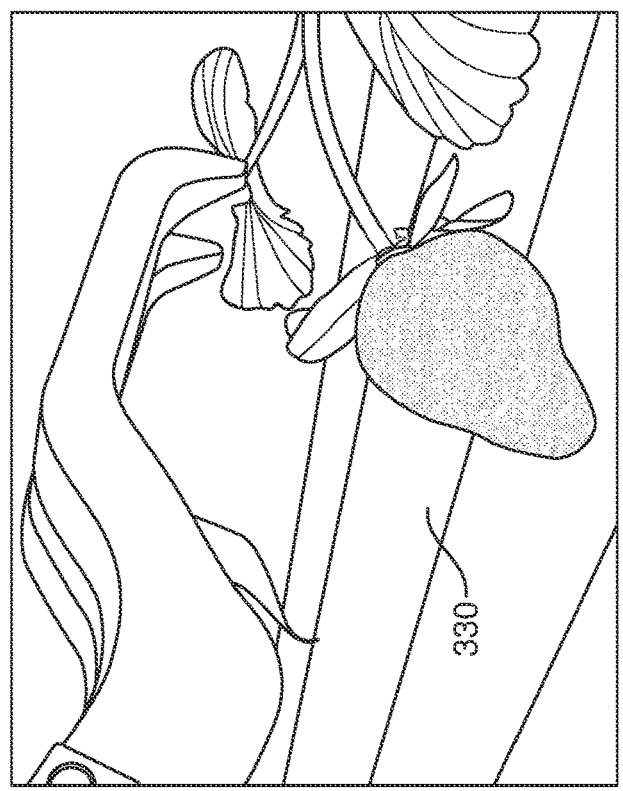
FIGS. 3D and 3E illustrate an end effector having a gripper with a hook-like shape, according to one or more embodiments.
Figure 3D:
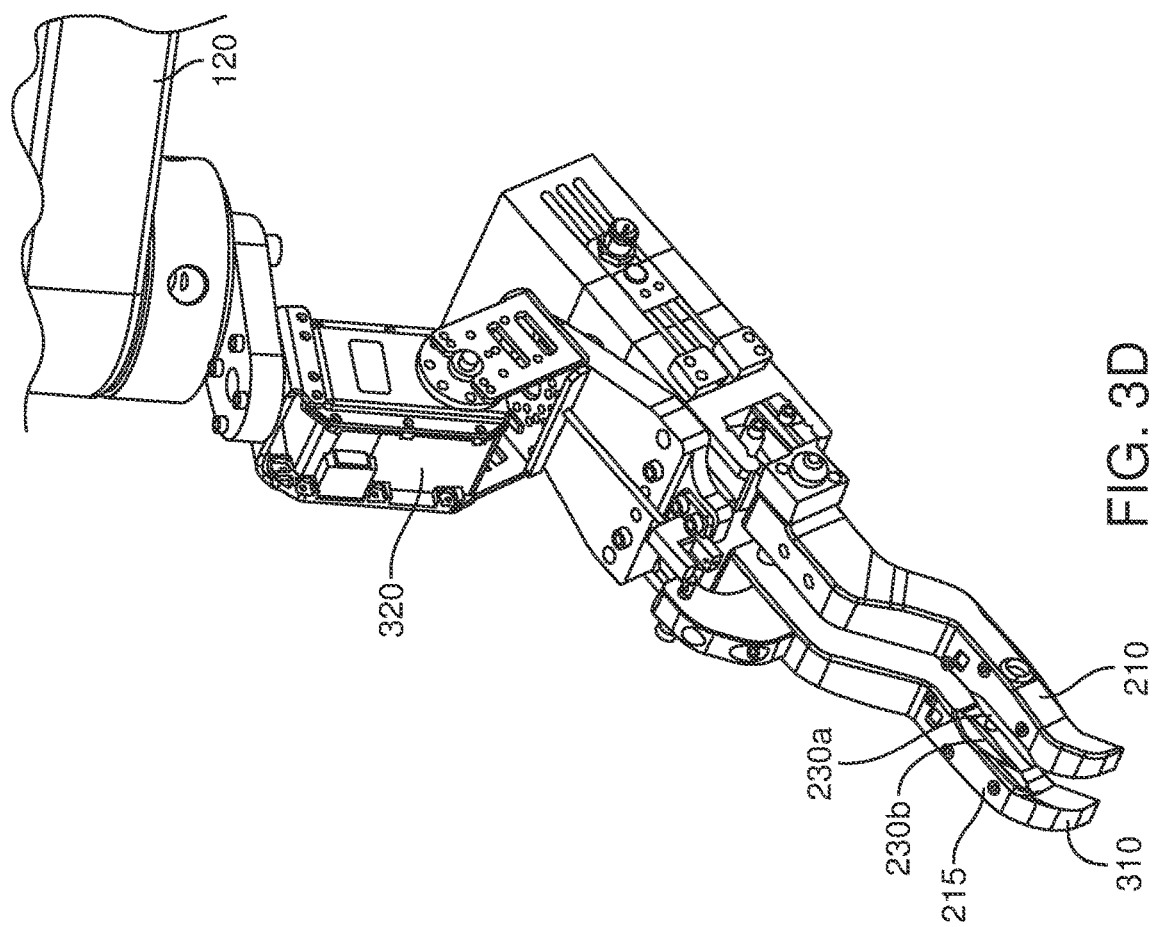

In some embodiments, depending on the application of the gripper, the shape of the various of the gripper may be different than the one depicted in FIGS. 2A through 2D. For example, when picking fruits or vegetables that do not hang vertically, the shape of the left gripper finger 210 and the right gripper finger 215 may be modified to facilitate access to the fruit or vegetable. FIGS. 3D and 3E illustrate an end effector having a gripper with a hook-like shape, according to one or more embodiments. The gripper shown in FIGS. 3D and 3E include a hook-like tip 310 that allows the gripper to grab onto a fruit or vegetable that is resting next to a surface (such as the edge of a support band 330) to manipulate the fruit or vegetable to position the gripper such that stem of the fruit or vegetable is accessible by the upper cutting element, the lower cutting element, and the holding member. In some embodiments, the hook-like tip includes a wedge like structure that is disposed at an angle with respect to the portions of the left gripper finger and the right gripper finger holding the upper cutting element and the lower cutting element.

In some embodiments, the gripper is mounted to the arm 120 by an axis actuator 320. The axis actuator 320 enables the gripper to rotate to allow the gripper to approach a fruit or vegetable at an angle. As such, the axis actuator 320 enables the gripper to access fruits or vegetables that are not hanging vertically from the plant. In some embodiment, the harvesting robot 100 determines an angle of a fruit or vegetable to be harvested, and activates the axis actuator 320 to rotate the gripper to an angle determined based on the determined angle of the fruit or vegetable. In some embodiments, the axis actuator is configured to rotate the gripper to control the pitch of the gripper. That is, the axis actuator may be configured to rotate the gripper along a transverse plane of the gripper to angle the gripper up or down based on an orientation of the fruit or vegetable to be harvested.

Figure 4B:
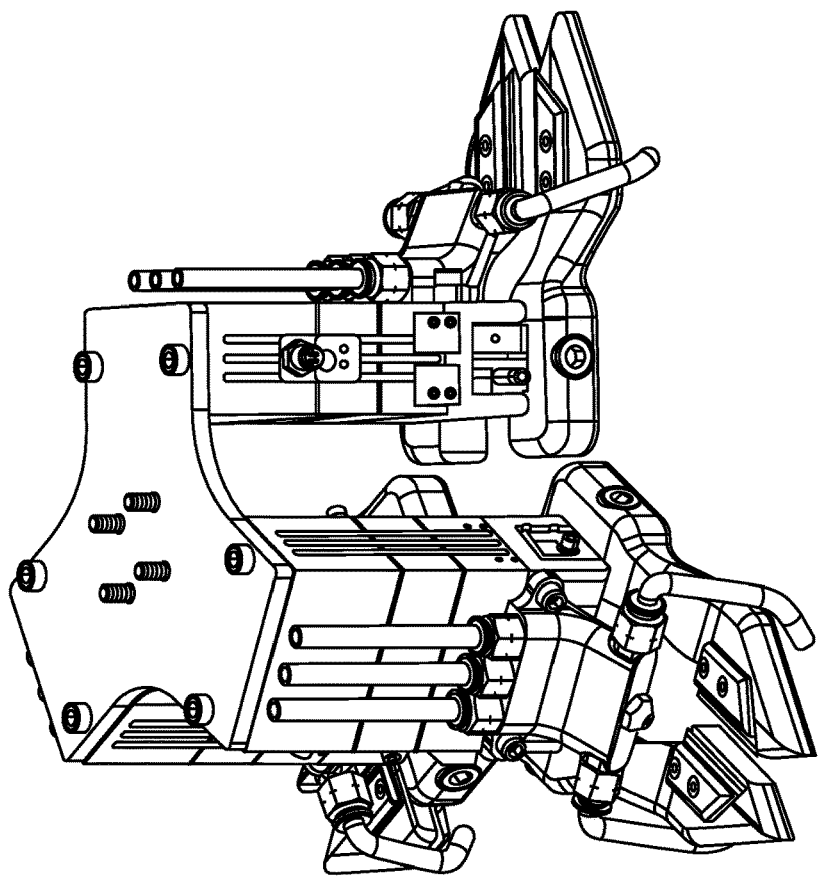
FIG. 4B illustrates a perspective view of an end-effector having three grippers, according to one or more embodiments.
Figure 4A:
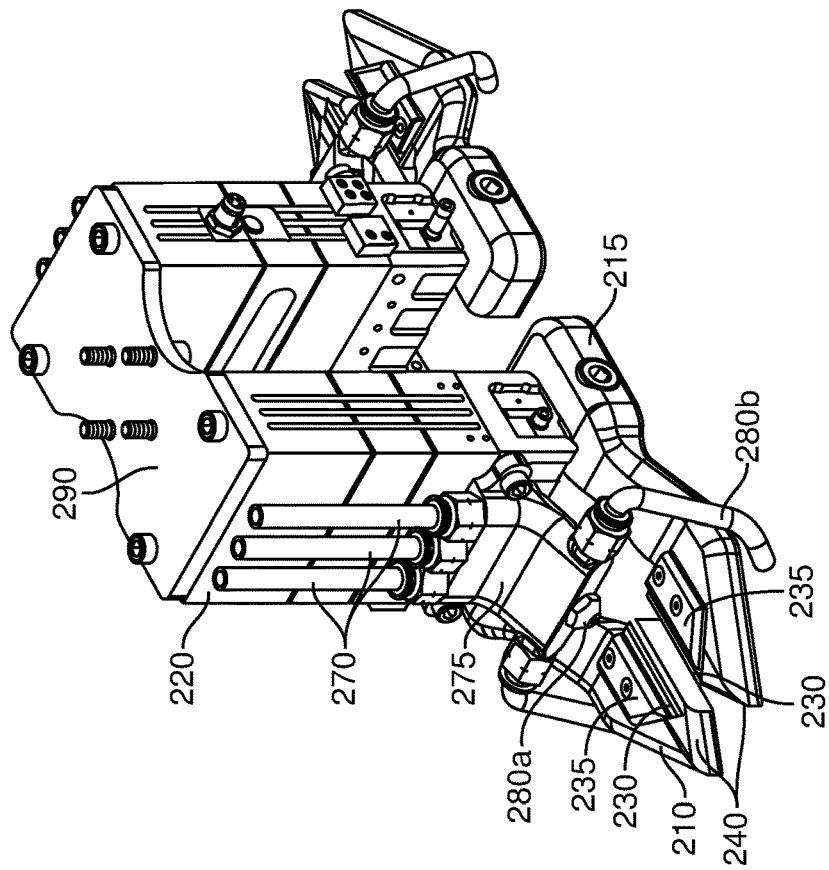
FIG. 4A illustrates a perspective view of an end-effector having two grippers, according to one or more embodiments.

In some embodiments, the end-effector 130 includes multiple grippers 200. FIG. 4A illustrates a perspective view of an end-effector having two grippers, according to one or more embodiments. FIG. 4B illustrates a perspective view of an end-effector having three grippers, according to one or more embodiments. In yet other embodiments, the end-effector 130 may have any other number of grippers 200. When multiple grippers are used, the end-effector may have a rotating base to enable all grippers to approach plants from various angles. The grippers 200 of the end-effector 130 may be rotated to enable the end-effector 130 to harvest multiple fruits or vegetables without having to move the end-effector to a collecting area for releasing the harvested fruits or vegetables. For example, the embodiments that includes two grippers 200 may be used to harvest two fruits or vegetables before having to move the end-effector to the collecting area for releasing the two harvested fruits or vegetables.

In some embodiment, the end-effector 130 includes and adapter plate 290. The geometry of the adapter plate can be modified to attach multiple grippers 200. The thickness of the adapter plate may vary depending on the number and the weight of the grippers that are getting mounted on the adapter plate. The material of the adapter plate may be chemical resistant and rust-free metal such as anodized aluminum or stainless steel.

Alternate Ejection Mechanisms

In some embodiments, different ejection mechanisms may be used instead of cutting the stem with the lower cutting element. For example, wedges may be used instead of blades to push the fruit or vegetable to detach the fruit or vegetable from the stem instead of cutting the stem to remove the stem from the fruit or vegetable. When blades are used to cut the stem to eject the harvested fruit or vegetable, a length of the stem may remain attached on top of the harvested fruit or vegetable which may add additional steps to remove the remaining stem before final packaging of the fruit or vegetable. By using different ejection mechanisms, the harvested fruit or vegetable can be pulled out from the stem reducing the likelihood that a small piece of the stem remains attached to the fruit or vegetable.

Figure 5A:
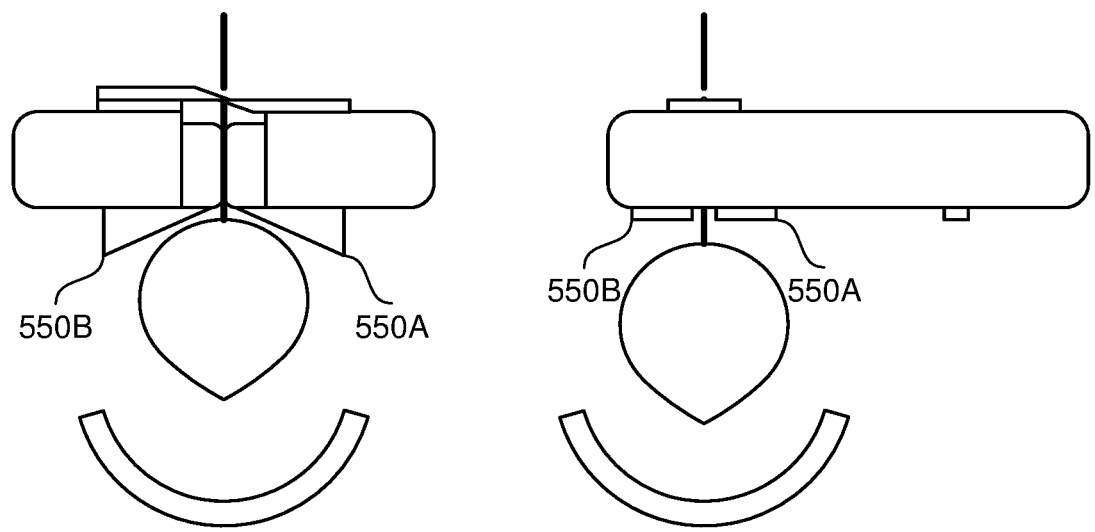
FIGS. 5A and 5B illustrate a gripper 200 having an ejection mechanism instead of the lower cutting element, according to one or more embodiments.
Figure 5B:
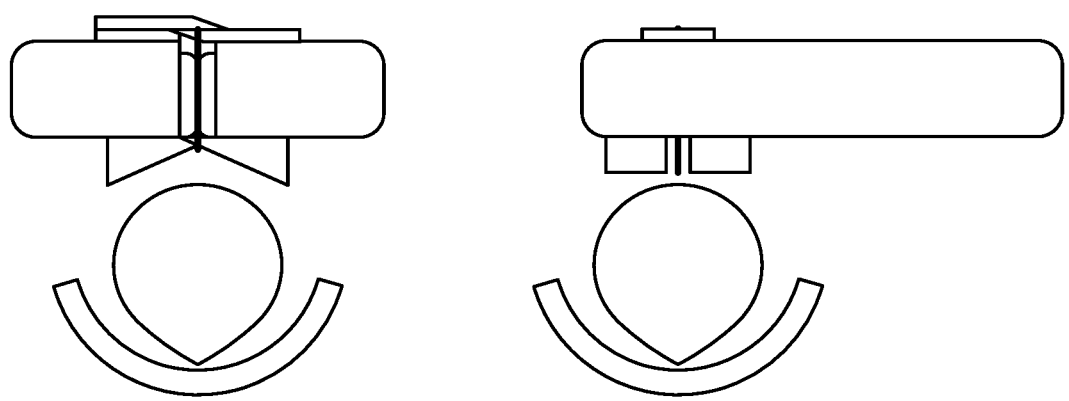

FIGS. 5A and 5B illustrate a gripper 200 having an ejection mechanism instead of the lower cutting element, according to one or more embodiments. FIG. 5A illustrates a front view (left portion of FIG. 5A) and a side view (right portion of FIG. 5A) of the gripper 200 having an ejection mechanism when the gripper is actuated to be at the first position (when the upper cutting element is engaged and the ejection mechanism is not engaged). FIG. 5B illustrates a front view (left portion of FIG. 5B) and a side view (right portion of FIG. 5B) of the gripper 200 having an ejection mechanism when the gripper is actuated to be at the second position (when the ejection mechanism is engaged). As shown in FIGS. 5A and 5B, the ejection system includes one or more wedges 550. For example, the ejection system may include a first wedge 550A attached to the left gripper finger 210 and a second wedge 550B attached to the right gripper finger 215. The wedges 550 may have angled surfaces to gently push onto a top surface of the harvested fruit or vegetable, causing the fruit or vegetable to detach from the stem. For example, the wedges 550 may have a triangular cross-section that is configured such that a distance between the wedges and the fruit or vegetable decreases as the gap between the left gripper finger 210 and the right gripper finger 215 is reduced. Once the angled surfaces of the wedges come in contact with the top surface of the fruit or vegetable, as the gap between the left gripper finger 210 and the right gripper finger 215 is further reduced, an ejecting force pushing the fruit or vegetable away from the stem is increased until the fruit or vegetable is detached from the stem. In some embodiments, the wedges may be made of a soft and food-safe material to be able to push gently on the fruit or vegetable without causing any damage.

Figure 6A:
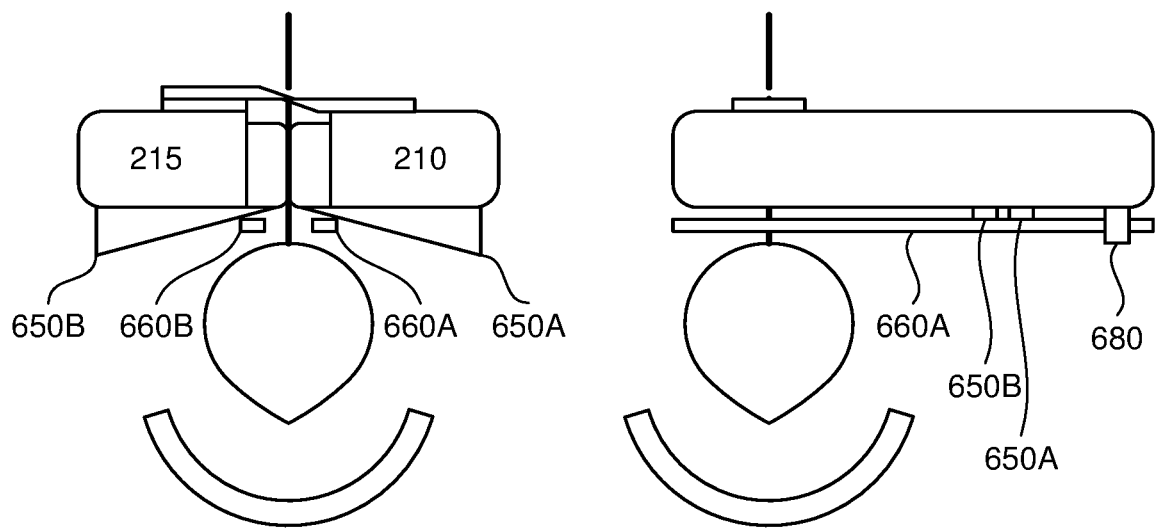
FIGS. 6A and 6B illustrate a gripper 200 having an ejection mechanism instead of the lower cutting element, according to one or more embodiments.
Figure 6B:
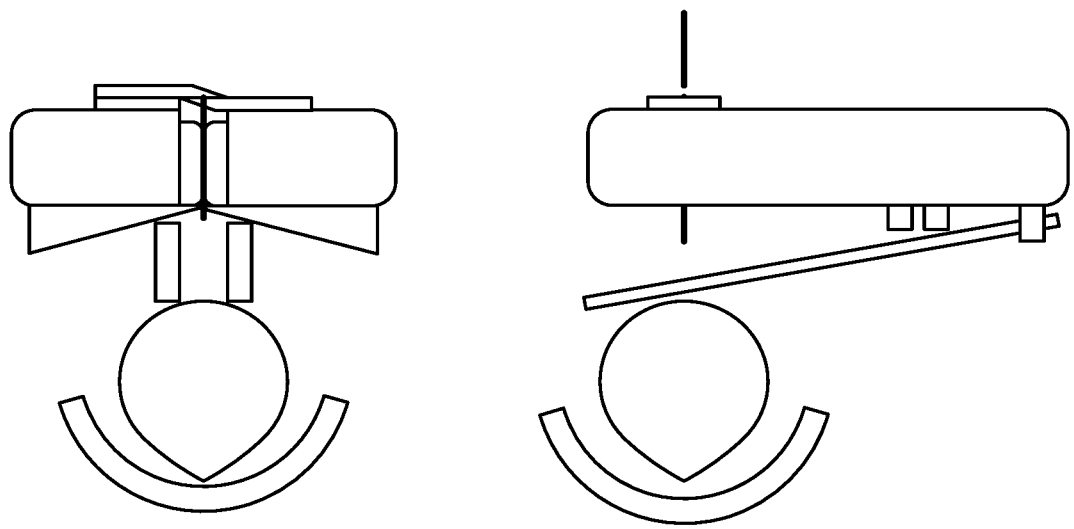

FIGS. 6A and 6B illustrate a gripper 200 having an ejection mechanism instead of the lower cutting element, according to another embodiment. FIG. 6A illustrates a front view (left portion of FIG. 6A) and a side view (right portion of FIG. 6A) of the gripper 200 having an ejection mechanism when the gripper is actuated to be at the first position (when the upper cutting element is engaged and the ejection mechanism is not engaged). FIG. 6B illustrates a front view (left portion of FIG. 6B) and a side view (right portion of FIG. 6B) of the gripper 200 having an ejection mechanism when the gripper is actuated to be at the second position (when the ejection mechanism is engaged). Specifically, the embodiments shown in FIGS. 6A and 6B include one or more levers 660 that are configured to rotate about a pivot point 680 and are actuated by one or more wedges 650. As such, in this embodiment, instead of having the wedges touch directly onto the harvested fruit or vegetable, the wedges 650 become fulcrums which push onto the levers 660 causing the levers to rotate about the pivot point 680. The rotation of the levers 660 about the pivot point 680 causes the levers to exert a force onto the harvested fruit or vegetable to cause the harvested fruit or vegetable to detach from the stem.

As shown in FIG. 6B, as the gripper fingers come closer to each other, the height of the wedges 650 right above the levers 660 increases. Once the height of the wedges 650 increases beyond the distance separating the levers 660 from the gripper fingers, the wedges 650 start exerting a downward force to the levers 660. The lever mechanism enables longer pushing distance and stronger pushing force with a smaller wedge dimension. In some embodiments, the levers 660 may be made of a soft and food-safe material which can push down on to the top of the harvested fruit or vegetable gently enough to reduce the likelihood of damaging the harvested fruit or vegetable.

In some embodiments, the wedges 650 are disposed between the harvested fruit and the pivot point 680 of the levers 660. However, the location of the wedges 650 may be adjusted to adjust the pushing force and distance of the levers 660. The closer the wedges 650 are to the pivot point 680, the stronger force and the longer distance of pushing onto the harvested fruit or vegetable.

As shown in FIGS. 5A-5B and 6A-6B, the gripper 200 having an ejection mechanism instead of the lower cutting element pushes down the top of the harvested fruit or vegetable to remove the stem without explicit clipping the stem, which may result in a smaller stem to remain attached to the fruit.

Harvesting Process Using Autonomous Harvesting Robot

Figure 7A:
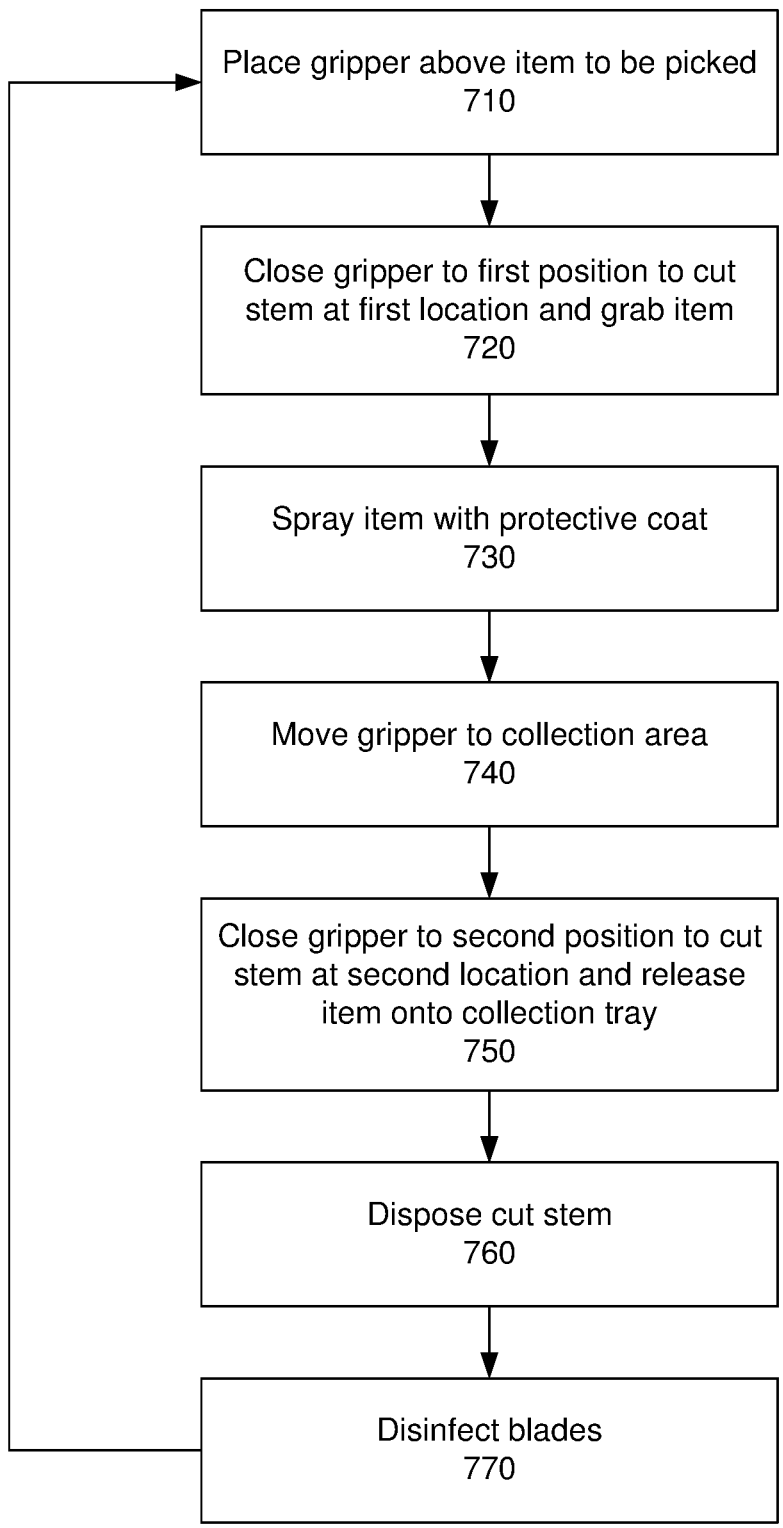
FIG. 7A illustrates a flow diagram of a process for harvesting produce using an autonomous robot having a gripper, according to one or more embodiments.

FIG. 7A illustrates a flow diagram of a process for harvesting produce using an autonomous robot having a gripper, according to one or more embodiments. Specifically, FIG. 7A illustrates a flow diagram for removing a fruit or vegetable from a plant. In some embodiments, a target fruit or vegetable is first identified, and the steps of FIG. 7A are performed for the identified target fruit or vegetable. The target fruit or vegetable may be identified using one or more sensors for determining the level of ripeness, size, or quality of the fruit or vegetable.

The gripper 200 of a robot 100 is placed 710 above the item (such as a fruit or vegetable) to be picked and around a stem connecting the item to be picked to the plant. In some embodiments, an arm of the robot is actuated to position the gripper 200 in place. The arm of the robot may be controlled based on one or more sensors, such as one or more cameras, depth sensors, infrared sensors, etc. In some embodiments, the sharp tips of the left and right arms of the gripper enables the gripper to enter through narrow gaps between stems. Depending on the location of different stems in the way of gripper's movement, the gripper may approach at different angles to avoid crashing into other stems. The fingers of the gripper may initially be in a closed or partially closed configuration to enter between stems, and may then be opened to push away any adjacent stems allowing the gripper to avoid grabbing more than one stem at a time. A physical stop (backend-stopper) may be mounted on the left and/or right finger for the gripper in order to compensate for inaccuracy of the position of the stem by limiting the position of the stem from going in too deep towards the gripper.

The gripper is partially closed 720 to the first position (e.g., by reducing a distance between the left gripper finger and the right gripper finger) to cut the stem at a first location by the upper cutting element of the gripper, thus detaching the item being harvested from the plant. Moreover, as the gripper is partially closed to the first position, the holding member of the gripper grabs onto the stem to hold the item being harvested. In some embodiments, the thickness of the stem is determined (e.g., using one or more sensors) to control the partial closing of the left and right fingers for cutting the stem. In some embodiments, the gripper includes a force sensor for sensing the force being applied to the stem to prevent damage to the stem as the stem is being cut by the upper cutting element.

If the end-effector 130 has two or more grippers 200, a second target fruit or vegetable is identified, the end-effector is rotated to enable the use of a second gripper, and steps 710 and 720 are repeated using the second gripper to harvest the second target fruit or vegetable. These steps are repeated for each gripper of the end-effector 130.

In some embodiments, the item being harvested is sprayed 730 with a protective coat to improve the quality of the item. For example, the nozzle 280A of the gripper 200 may spray a chemical or a mixture of chemicals configured to clean and/or disinfect the item being harvested. The direction of the nozzles may be oriented using the robot's arm to apply the same chemicals to the live plant as well. Nozzles 280B on the sides of the grippers 200 may apply different types of protective coats or nutrients to harvested fruits or vegetables in order to help the harvested fruit or vegetable to last longer and maintain its flavor for a longer time.

The gripper is moved 740 to a collection area. The collecting area may include a collection tray for collecting the items being harvested. In some embodiments, the robot 100 selects a collection slot within a collection tray and positions the gripper above the selected collection slot. In some embodiments, the length of the item being harvested may be measured (e.g., using computer vision or one or more other sensors). Based on the determined size of the item being harvested (and optionally based on the weight of the item being harvested), the robot 100 may determine a distance between the item being harvested and the collection slot. For example, the robot 100 may determine whether the bottom of the item being harvested is in contact with surface of the collection slot.

Once the gripper is positioned above a selected collection slot, the gripper is closed 750 to a second position to cut the stem of the item being harvested at a second location. By cutting the stem of the item being harvested at the second location, the item being harvested is released from the gripper, thus placing the item being harvested in the collection slot. Alternatively, the gripper may release the item being harvested by opening gripper (i.e., by increasing a distance between the left gripper finger and the right gripper finger).

If the end-effector 130 has two or more grippers 200, steps 740 and 750 are repeated for each gripper of the end-effector 130. That is, a second gripper 200 is positioned above a second collection slot and the second gripper is closed to the second position to release the second item being harvested to release the second item from the second gripper.

In some embodiments, the gripper continues to hold (by the holding member) the stem that was previously attached to the item being harvested. The gripper then disposes 760 the stem by opening the gripper above a disposal bin.

The blades of gripper (such as the blades of the upper cutting element and the blades of the lower cutting element) are disinfected 770. For instance, cleaning or disinfecting chemicals are dispensed through the nozzles 280A of the disinfecting module. The blades of the gripper are disinfected to reduce the risk of contaminating the live plant during the next harvesting operation. In some embodiments, the disinfecting chemicals are also applied to other equipment on and off the robot 100 by controlling the direction of the nozzle using the robot's arm. The disinfecting module may be capable of applying various sanitizing chemicals including, but not limited to hydrogen peroxide, peroxyacetic acid, diluted sulfuric acid, and bleach. These chemicals may be applied to the blades of the gripper before and after each cutting operation.

FIGS. 7B through 7E illustrate front views of the gripper 200 at various stages in the process for harvesting produce of FIG. 7A. FIG. 7B illustrates a front view of the gripper 200 in the open configuration after being positioned above the item being harvested during step 710 of FIG. 7A, according to one or more embodiments. As shown in FIG. 7B, the left gripper finger 210 of the gripper is positioned to the left of the stem 785 that is attached to the item being harvested 780, and the right gripper finger 215 is positioned to the right of the stem 785. In some embodiments, during step 710 of FIG. 7A, the gripper 200 is positioned such that the blades 250 of the lower cutting element are positioned just above the item being harvested 780.

FIG. 7C illustrates a front view of the gripper 200 partially closed to the first position during step 720 of FIG. 7A, according to one or more embodiments. Specifically, to control the gripper to be in the configuration shown in FIG. 7C, the actuator 220 is activated to move the left gripper finger 210 and/or the right gripper finger 215 such that the gap between the left gripper finger 210 and the right gripper finger 215 is reduced until the blades 230 of the upper cutting element are engaged. In the configuration shown in FIG. 7C, the blades 230 of the upper cutting element are engaged, causing the stem 785 to be cut at the first location 795A, detaching the item being harvested 780 from the plant. In addition, in the configuration shown in FIG. 7C, when the gripper is partially closed to the first position, the left compliant element 240A and the right compliant element 240B are engaged with each other, causing the left compliant element 240A and the right compliant element 240B to compress, causing the holding member to securely grab the cut stem. Moreover, in the configuration shown in FIG. 7C, the blades 250 of the lower cutting element are not yet engaged, thus, allowing the item being harvested 780 to remain attached to the portion of the stem being grabbed by the holding member (i.e., by the left compliant element 240A and the right compliant element 240B).

FIG. 7D illustrates a front view of the gripper 200 closed to the second position during step 750 of FIG. 7A, according to one or more embodiments. In the configuration shown in FIG. 7D, the blades 250 of the lower cutting element are engaged, causing the stem 785 to be cut at the second location 795B, detaching the item being harvested 780 from the stem. As such, the item being harvested 780 is dropped in the collection slot 790, while the gripper 200 keeps holding the cut stem. In some embodiments, as the left gripper finger 210 and the right gripper finger 215 are further closed from the first position (where the blades 230 of the upper cutting element are engaged but the blades 250 of the lower cutting element are not engaged) to the second position (where both the blades 230 of the upper cutting element and the blades 250 of the lower cutting element are engaged), the compliant elements of the holding member are further compressed.

FIG. 7E illustrates a front view of the gripper 200 disposing the cut stem during step 760 of FIG. 7A, according to one or more embodiments. To release the cut stem, the left gripper finger 210 and the right gripper finger 215 are separated, opening holding member. That is, as the distance between the left gripper finger 210 and the right gripper finger 215 is increased, the pressure applied by the left compliant element 240A and the right compliant element 240B decreases, decreasing a friction holding the stem, until the stem is released from the gripper 200.

Figure 8A:
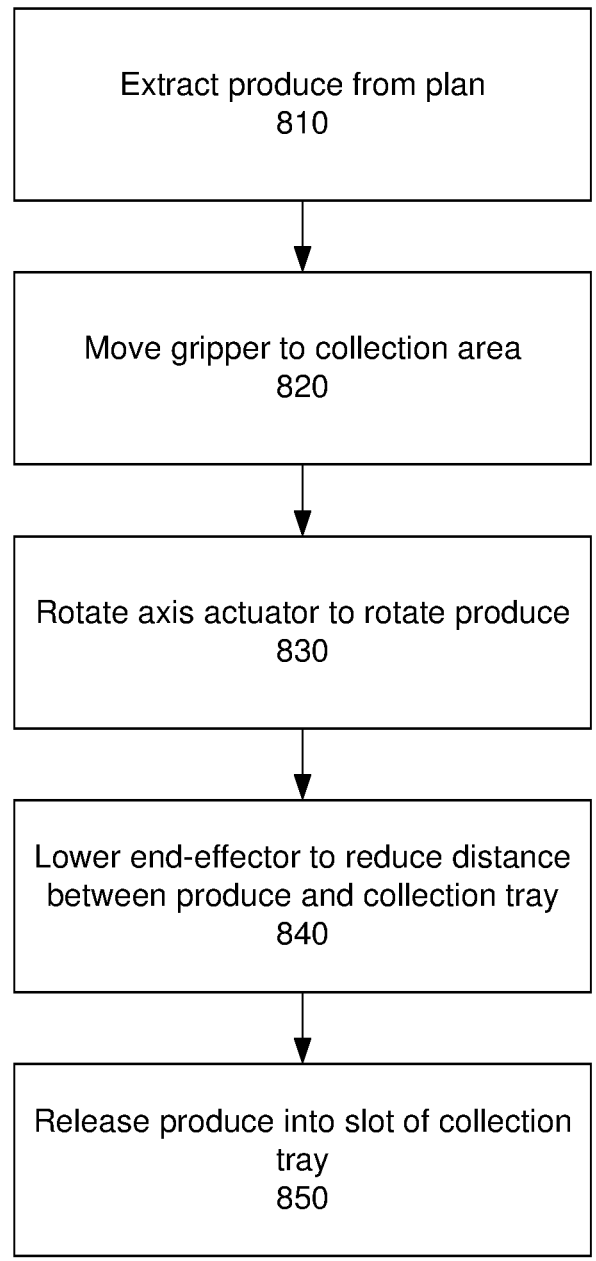
FIG. 8A illustrates a flow diagram of a process for transferring a harvested produce to a collection tray, according to one or more embodiments.

FIG. 8A illustrates a flow diagram of a process for transferring a harvested produce to a collection tray, according to one or more embodiments. In this embodiment, the end-effector 130 is coupled to the arm 120 of the harvesting robot 100 through an axis actuator 880. The axis actuator 880 allows the angle of the end-effector 130 (and thus, the angle of the gripper 200 of the end-effector) to be actuated to change the angle of the fruit or vegetable being held by the gripper. Specifically, the angle of the gripper 200 can be controlled such that an angle between a side surface of the fruit or vegetable being harvested and a bottom surface of a slot of the collection tray.

Figure 8C:
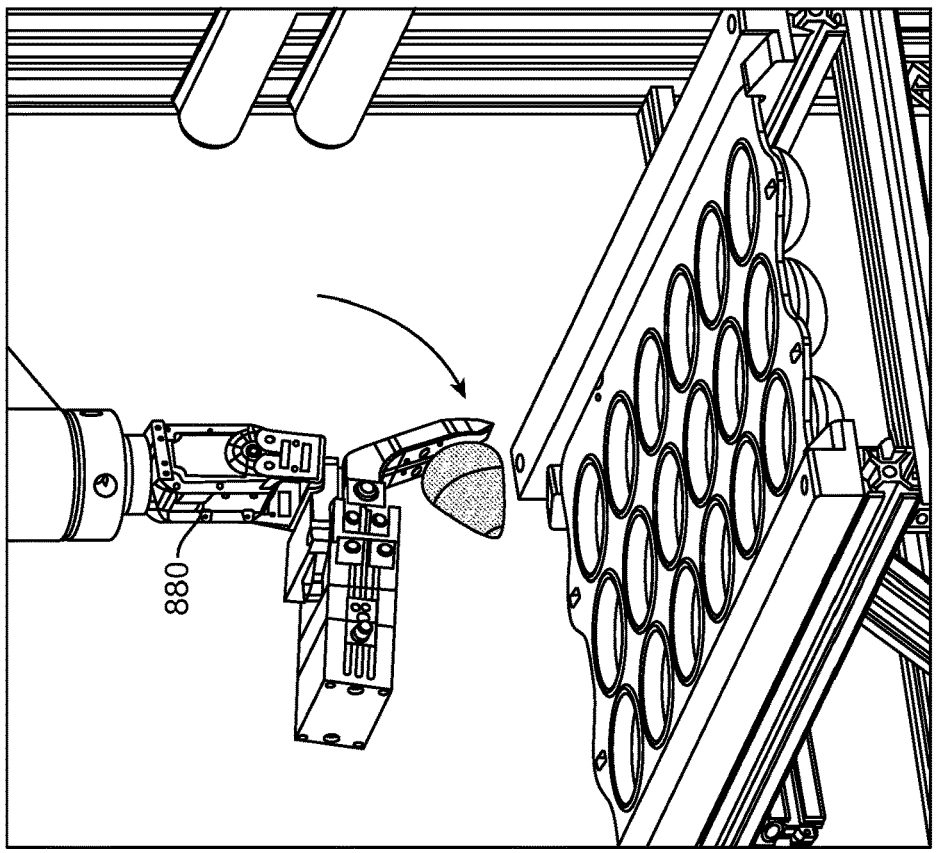
FIGS. 8B through 8E illustrate perspective views of the gripper at various stages in the process for transferring a harvested produce to a collection tray of FIG. 8A.
Figure 8B:
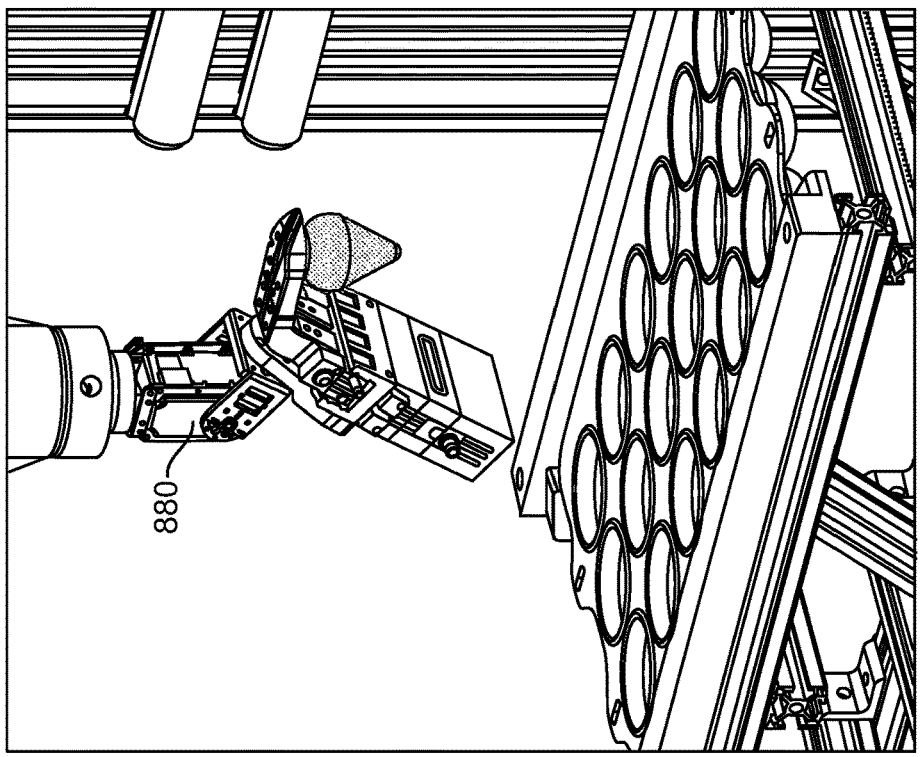

The gripper 200 of an end-effector of a robot 100 extracts 810 an item (such as a fruit or vegetable) from a plant and the gripper 200 is moved 820 to position the gripper above a collection tray. In some embodiments, the robot 100 identifies a slot within the collection tray and moves the gripper to position the gripper above the selected slot. The robot 100 may move the gripper 200 by actuating the arm 120 coupled to the end-effector 130 that includes the gripper 200 holding the fruit or vegetable. A perspective view of a gripper positioned above a selected slot of a collection tray is illustrated in FIG. 8B.

Once the gripper 200 is positioned above a selected slot within the collection tray, the axis actuator 880 coupling the end-effector 130 to the arm 120 is rotated 830 to rotate the gripper 200, thus rotating the fruit or vegetable being held by the gripper 200. In some embodiments, the axis actuator 880 is activated to rotate the fruit such that an angle between the side surface of the fruit or vegetable and the bottom surface of the slot for depositing the fruit or vegetable is reduced. For example, the axis actuator 880 may be activated to rotate the fruit such that the side surface of the fruit or vegetable is parallel to the bottom surface of the slot. In some embodiments, the axis actuator is configured to rotate the gripper to control the pitch of the gripper. That is, the axis actuator may be configured to rotate the gripper along a transverse plane of the gripper to angle the gripper up or down to align the side surface of the fruit or vegetable to the bottom surface of the slot. In some embodiments, the amount of rotation is determined based on a type of fruit or vegetable being harvested. Alternatively, the amount of rotation is determined based on one or more sensors for determining an angle between the side surface of the fruit or vegetable and the bottom surface of the slot. A perspective view of a gripper after being rotated to reduce the angle between the side surface of the fruit or vegetable and the bottom surface of the slot of the collection tray is illustrated in FIG. 8C.

Figure 8E:
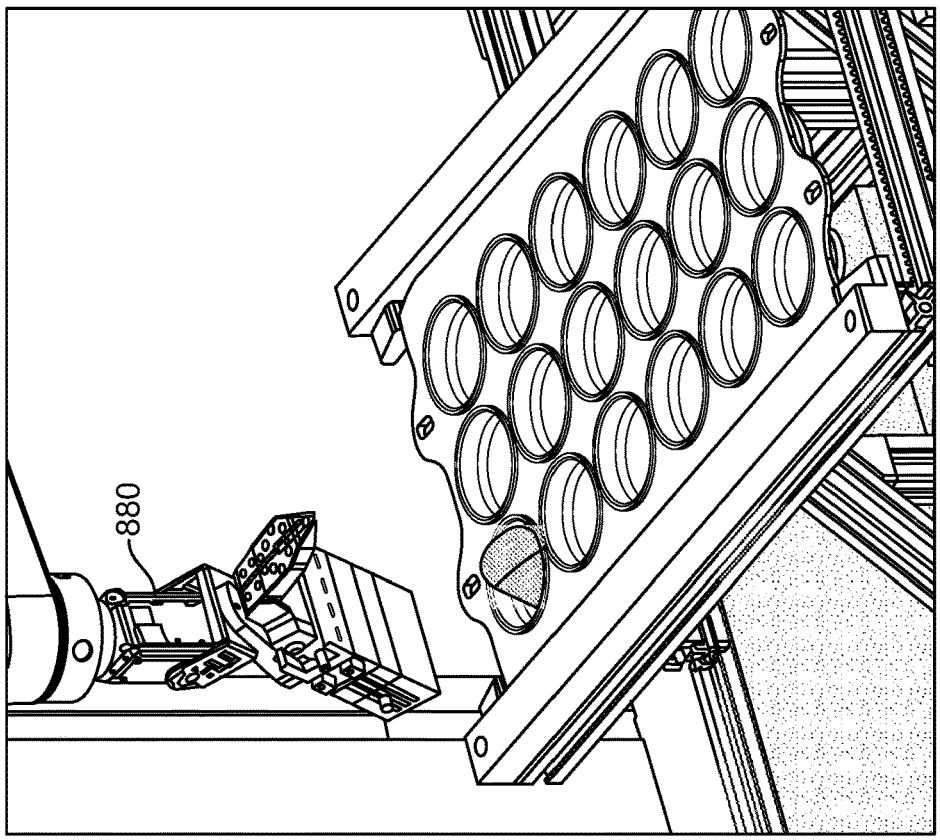
Figure 8D:
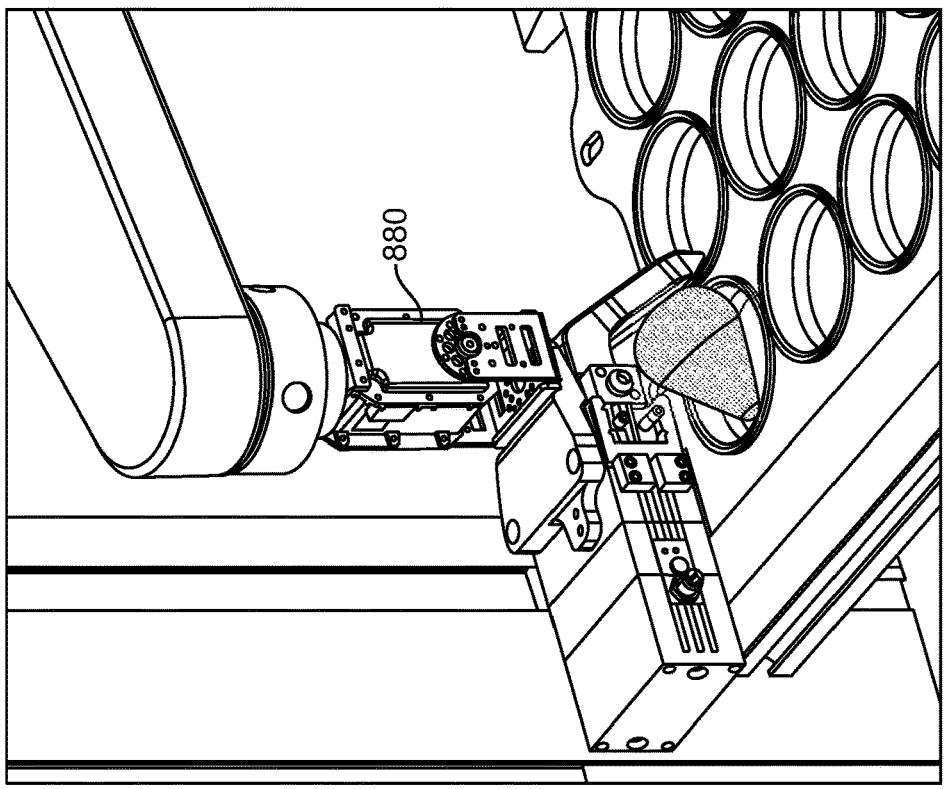

After the end-effector 130 has been rotated to reduce an angle between a side surface of the fruit or vegetable and bottom surface of the slot of the collection tray, the end-effector 130 is lowered 840 to reduce a distance between the fruit or vegetable and the bottom surface of the slot of the collection tray. In some embodiments, the arm 120 of the harvesting robot 100 is actuated to lower the end-effector 130. Moreover, in some embodiments, the end-effector is lowered until the side surface of the fruit or vegetable is in contact with the bottom surface of the slot of the collection tray. A perspective view of a gripper positioned such that the side surface of the fruit or vegetable is in contact with the bottom surface of the slot of the collection tray is illustrated in FIG. 8D.

Once the end-effector 130 has been lowered, the fruit or vegetable is released 850 into the slot of the collection tray. In some embodiments, the stem of the fruit or vegetable is cut using a lower cutting element of the gripper 200. In other embodiments, the fruit or vegetable is removed from the stem by pushing the fruit or vegetable (e.g., by using a wedge or a lever). A perspective view of a gripper after the fruit or vegetable has been released is illustrated in FIG. 8E.

Figure 9C:
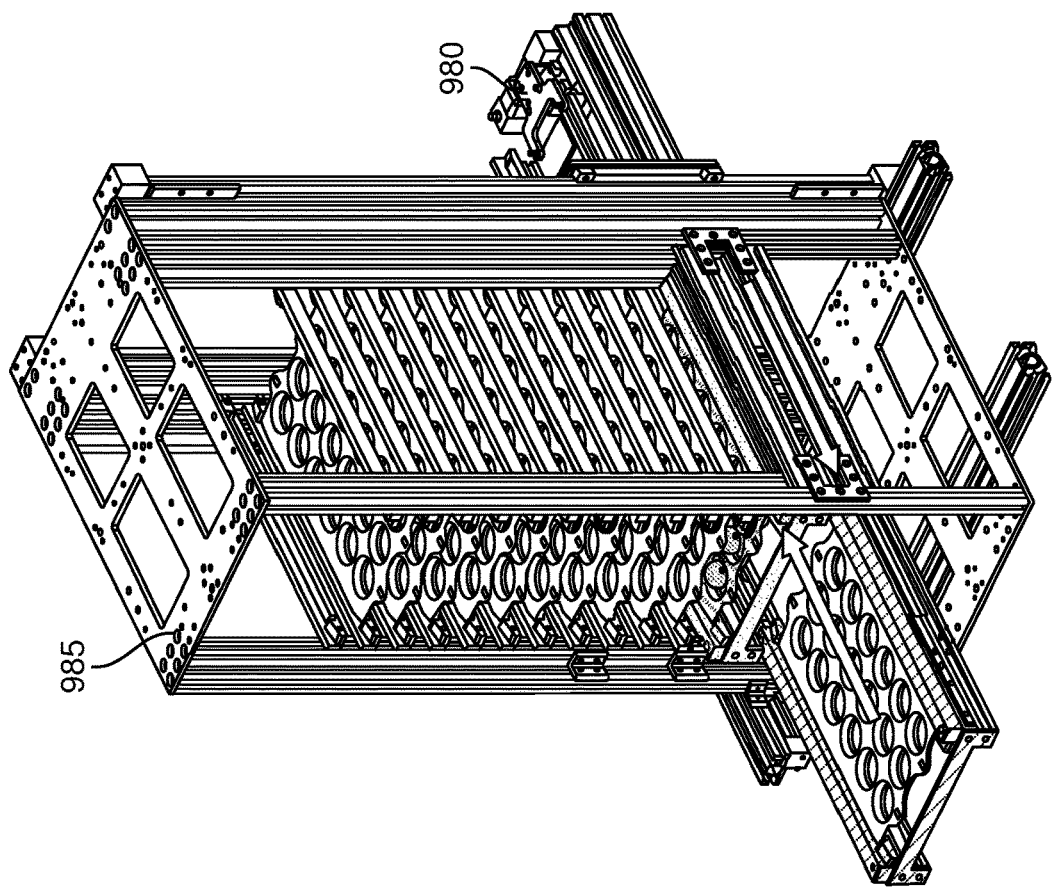
FIGS. 9B through 9F illustrate perspective views of the collection tray cycler at various stages in the process of cycling through collection trays of FIG. 9A.

FIG. 9A illustrates a flow diagram of a process for cycling through collection trays, according to one or more embodiments. In this embodiment, as shown in FIGS. 9B-9E, the harvesting robot 100 includes a collection tray cycler 980 for cycling through a set of collection trays 140. Moreover, the harvesting robot 100 may include a tray stacker 985 for holding the set of collection trays 140. The tray stacker 985 may have a set of slots, each capable of holding a collection tray 140. The collection tray cycler 980 may be capable of moving collection trays in and out of the slots of the tray stacker 985, and to swap collection trays from one slot of the tray stacker 985 to another slot of the tray stacker.

Figure 9B:
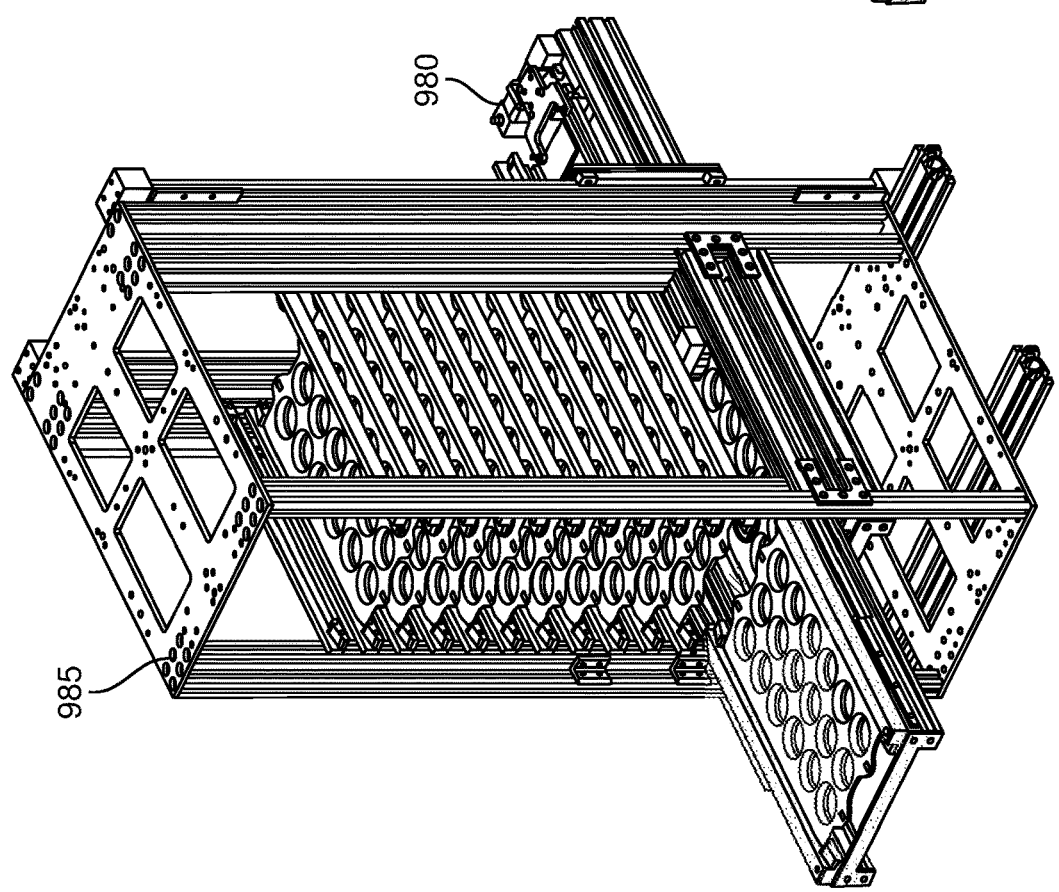

Referring to FIG. 9A, the collection tray cycler 980 presents 910 an empty tray in a first slot of the tray stacker 985. In some embodiments, if the first slot is empty, the collection tray cycler 980 may retrieve a collection tray from another slot of the tray cycler 980 and moves the collection tray to the first slot of the tray stacker 985. In some embodiments, the tray cycler 980 presents the collection tray in the first slot of the tray stacker 985 by pushing (or pulling) the collection tray to a collection area to enable the harvesting robot to place harvested items or produce on the collection tray. A perspective view of the tray stacker 985 and the collection tray cycler 980 presenting the collection tray in the first slot to enable the harvesting robot to place harvested items on the collection tray is illustrated in FIG. 9B.

Referring back to FIG. 9A, once the tray in the first slot is presented, the harvesting robot fills 915 the collection tray with harvested fruits or vegetables (e.g., as described and illustrated in the process of FIG. 7A). Once the collection tray in the first slot is full, the collection tray cycler 980 retracts 920 the collection tray in the first slot and presents an empty collection tray in the second slot of the tray stacker 985. In some embodiments, if the second slot is empty, the collection tray cycler 980 may retrieve a collection tray from another slot of the tray cycler 980 and moves the collection tray to the second slot of the tray stacker 985 while the harvesting robot is filling the collection tray in the first slot of the tray stacker 985. A perspective view of the tray stacker 985 and the collection tray cycler 980 retracting the collection tray in the first slot and presenting the collection tray in the second slot to enable the harvesting robot to place harvested items on the collection tray of the second slot is illustrated in FIG. 9C.

Figure 9E:
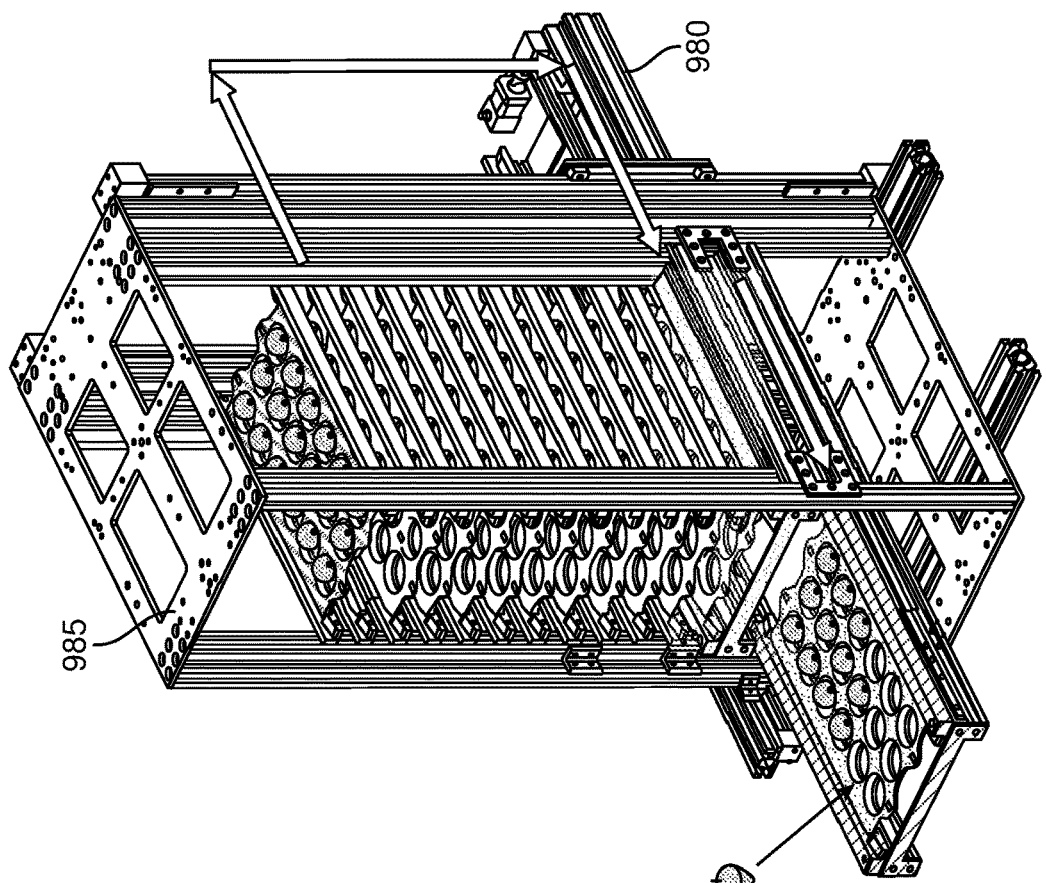
Figure 9D:
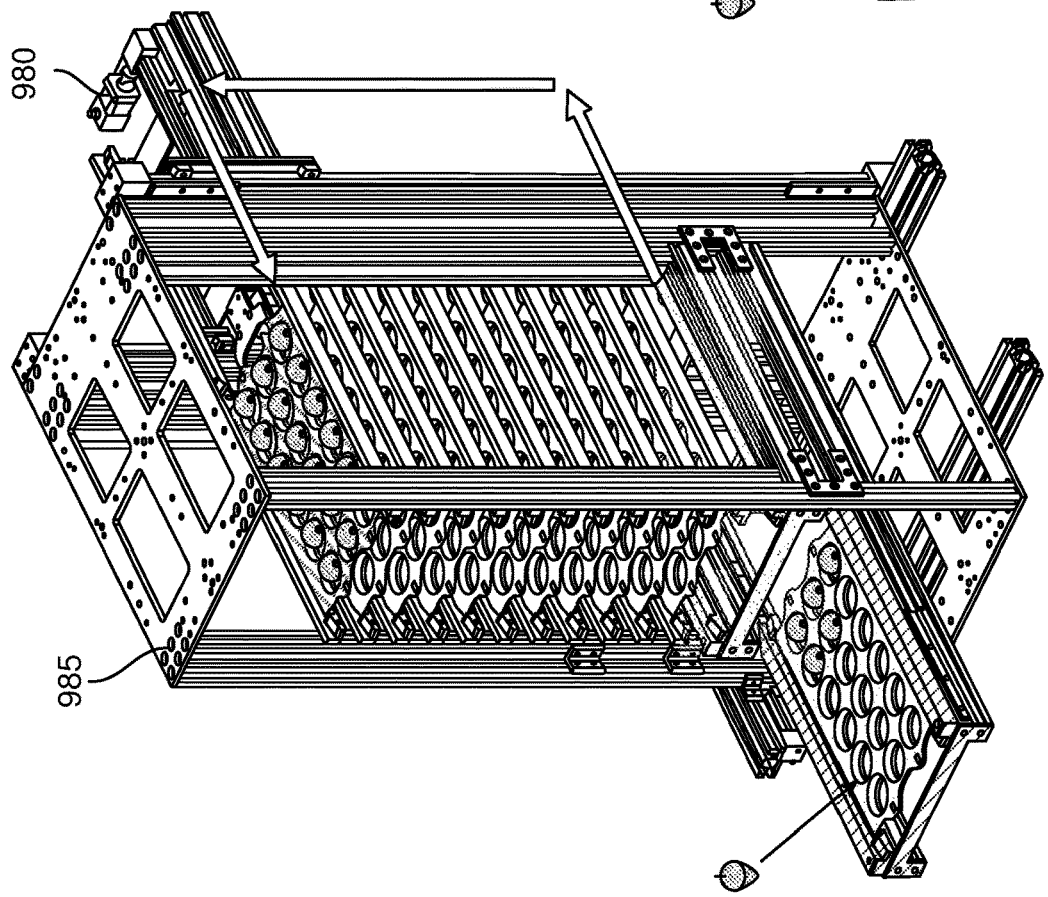

Referring back to FIG. 9A, once the tray in the second slot is presented, the harvesting robot fills 925 the collection tray with harvested fruits or vegetables (e.g., as described and illustrated in the process of FIG. 7A). Moreover, while the harvesting robot fills the collection tray of the second slot, the collection tray cycler 980 moves 930 the collection tray in the first slot to an empty slot and moves 935 an empty tray to the first slot. In some embodiments, the collection tray cycler 980 moves the tray in the first slot by pulling the tray out of the tray stacker 985, moves the collection tray to align the collection tray to a destination slot, and pushes the collection tray onto the destination slot in the tray stacker 985. A perspective view of the tray stacker 985 and the collection tray cycler 980 moving the collection tray in the first slot to an empty slot is illustrated in FIG. 9D. A perspective view of the tray stacker 985 and the collection tray cycler 980 moving an empty collection tray to the first slot is illustrated in FIG. 9E.

Figure 9F:
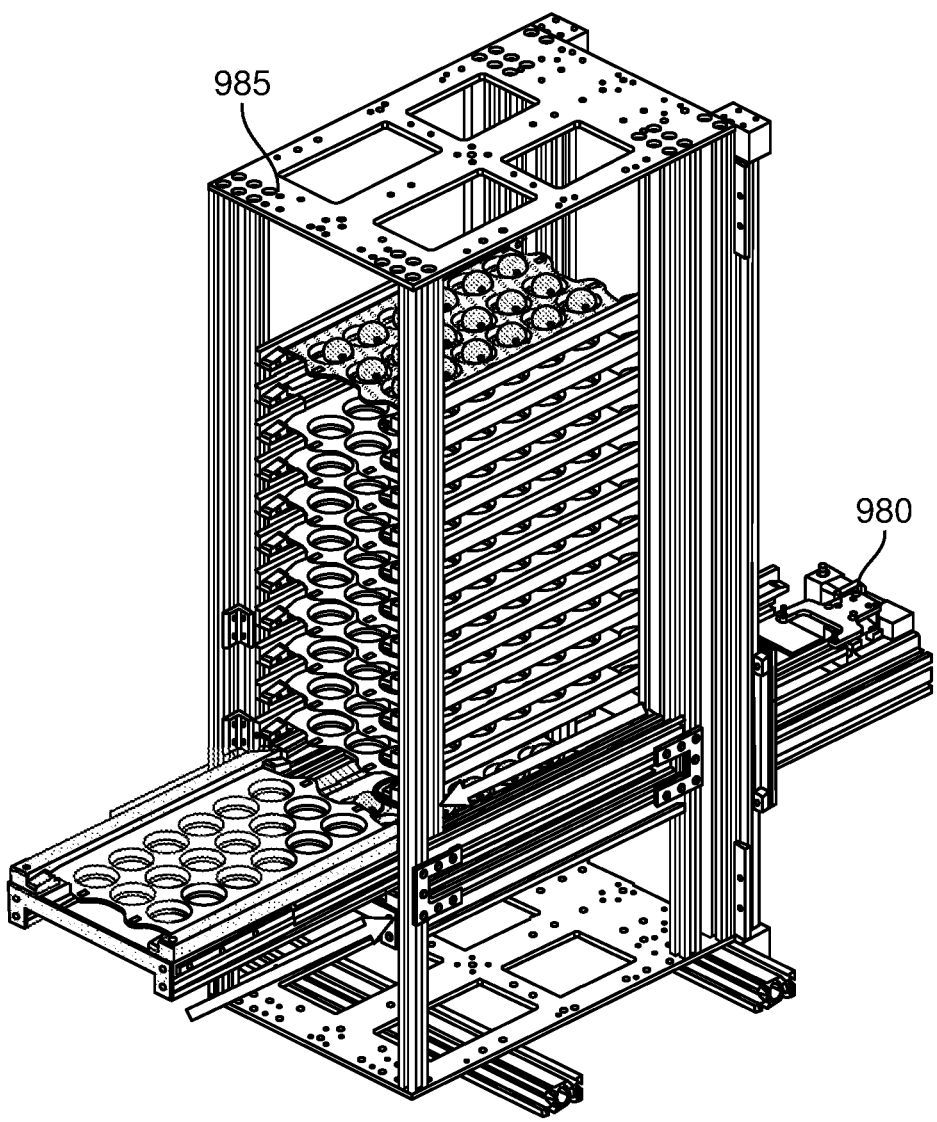

Referring back to FIG. 9A, once the collection tray in the second slot is full, the collection tray cycler 980 retracts 950 the collection tray in the second slot and presents the empty collection tray in the first slot of the tray stacker 985. Since the collection tray cycler 980 moved the filled collection tray that was in the first slot into an empty slot of the tray stacker 985 and replaced the filled collection tray with an empty collection tray while the harvesting robot was working to fill the collection tray of in second slot of the tray stacker 985, the collection tray cycler 980 is able to present an empty tray in the first slot without significant down time. A perspective view of the tray stacker 985 and the collection tray cycler 980 retracting the collection tray in the second slot and presenting the empty collection tray in the first slot to enable the harvesting robot to place harvested items on the collection tray of the first slot is illustrated in FIG. 9F.

Referring back to FIG. 9A, this process is repeated until all the collection trays in the tray stacker 985 are filled. For example, once the tray in the first slot is presented, the harvesting robot fills 955 the collection tray with harvested fruits or vegetables (e.g., as described and illustrated in the process of FIG. 7A). Moreover, while the harvesting robot fills the collection tray of the first slot, the collection tray cycler 980 moves 960 the collection tray in the second slot to an empty slot and moves 965 an empty tray to the second slot. This allows the collection tray cycler 980 to cycle through collection trays without significant down time to swap collection trays as they are filled by the harvesting robot.

Additional Considerations

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations or transformation of physical quantities or representations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device (such as a specific computing machine), that manipulates and transforms data represented as physical (electronic) quantities within the computer system memories or registers or other such information storage, transmission or display devices.

Certain aspects of the embodiments include process steps and instructions described herein in the form of an algorithm. It should be noted that the process steps and instructions of the embodiments can be embodied in software, firmware or hardware, and when embodied in software, could be downloaded to reside on and be operated from different platforms used by a variety of operating systems. The embodiments can also be in a computer program product which can be executed on a computing system.

The embodiments also relate to an apparatus for performing the operations herein. This apparatus may be specially constructed for the purposes, e.g., a specific computer, or it may comprise a computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Memory can include any of the above and/or other devices that can store information/data/programs and can be transient or non-transient medium, where a non-transient or non-transitory medium can include memory/storage that stores information for more than a minimal duration. Furthermore, the computers referred to in the specification may include a single processor or may be architectures employing multiple processor designs for increased computing capability.

The algorithms and displays presented herein are not inherently related to any particular computer or other apparatus. Various systems may also be used with programs in accordance with the teachings herein, or it may prove convenient to construct more specialized apparatus to perform the method steps. The structure for a variety of these systems will appear from the description herein. In addition, the embodiments are not described with reference to any particular programming language. It will be appreciated that a variety of programming languages may be used to implement the teachings of the embodiments as described herein, and any references herein to specific languages are provided for disclosure of enablement and best mode.

Throughout this specification, some embodiments have used the expression "coupled" along with its derivatives. The term "coupled" as used herein is not necessarily limited to two or more elements being in direct physical or electrical contact. Rather, the term "coupled" may also encompass two or more elements are not in direct contact with each other, but yet still co-operate or interact with each other, or are structured to provide a thermal conduction path between the elements.

Likewise, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of embodiments. This description should be read to include one or at least one and the singular also includes the plural unless it is obvious that it is meant otherwise. The use of the term and/or is intended to mean any of: "both", "and", or "or."

In addition, the language used in the specification has been principally selected for readability and instructional purposes, and may not have been selected to delineate or circumscribe the inventive subject matter. Accordingly, the disclosure of the embodiments is intended to be illustrative, but not limiting, of the scope of the embodiments.

While particular embodiments and applications have been illustrated and described herein, it is to be understood that the embodiments are not limited to the precise construction and components disclosed herein and that various modifications, changes, and variations may be made in the arrangement, operation, and details of the methods and apparatuses of the embodiments without departing from the spirit and scope of the embodiments.

What is claimed is:

1. A device for harvesting produce from a plant comprising:
   a base;
   an arm coupled to the base; and
   an end-effector coupled to the arm, the end-effector comprising one or more grippers, at least one gripper of the one or more grippers comprising:
      a first finger and a second finger extending in a first direction, the first finger and the second finger coupled to an actuator that is configured to increase or decrease a distance between the first finger and the second finger,
      a first cutter including a first blade attached to the first finger and a second blade attached to the second finger and configured to cut a stem of the produce at a first location,
      a second cutter including a third blade attached to the first finger and a fourth blade attached to the second finger and configured to cut the stem of the produce at a second location closer to the produce than the first location,
      a holding member including a first compliant element attached to the first finger and a second compliant element attached to the second finger, the first and second compliant elements configured to move toward each other in a second direction that intersects the first direction and plastically deform to hold the stem of the produce, the holding member disposed between the first cutter and the second cutter, and
      a first tip and a second tip opposingly angled away from each other and located at a distal end of the first finger and the second finger, respectively, the first tip and second tip configured to guide the stem of the produce inwardly and between the first and second fingers to be accessible by the holding member.

2. The device of claim 1, wherein the first blade of the first cutter is disposed on a first side of the first finger, the third blade of the second cutter is disposed on a second side of the first finger, opposite to the first side, the second blade of the first cutter is disposed on the first side of the second finger, and the fourth blade of the second cutter is disposed on the second side of the second finger.

3. The device of claim 1, wherein the first blade of the first cutter is configured to engage with the second blade of the first cutter when the distance between the first finger and the second finger is smaller than a first distance, and wherein the third blade of the second cutter is configured to engage with the fourth blade of the second cutter when the distance between the first finger and the second finger is smaller than a second distance, the second distance smaller than the first distance.

4. A device for harvesting produce from a plant comprising:
 a base;
 an arm coupled to the base;
 an end-effector coupled to the arm, the end-effector comprising one or more grippers, at least one gripper of the grippers comprising:
  a first cutter configured to cut a stem of the produce at a first location,
  a second cutter configured to cut the stem of the produce at a second location closer to the produce than the first location,
  a holding member configured to plastically deform to hold the stem of the produce, the holding member disposed between the first cutter and the second cutter; and
  a disinfecting module comprising:
   one or more tubes configured to deliver one or more chemicals,
   one or more nozzles for spraying the one or more chemicals, and
   a chemical distributer coupled between the one or more tubes and the one or more nozzles, the chemical distributer configured to control a flow of the one or more chemicals from the one or more tubes to the one or more nozzles,
  wherein the one or more nozzles comprises:
   a first nozzle for spraying the one or more chemicals to at least the first and second cutter, and
   a second nozzle for spraying the one or more chemicals to the produce harvested by the at least one gripper.

5. The device of claim 1, wherein the first cutter is configured to cut the stem of the produce at the first location to detach the produce from the plant, and wherein the second cutter is configured to cut the stem of the produce at the second location to remove the stem from the produce.

6. The device of claim 1, wherein the arm is configured to move the end-effector to position a gripper of the one or more grippers of the end-effector around the stem of the produce.

7. The device of claim 1, further comprising:
 one or more collection trays for collecting the produce harvested from the plant, wherein the arm is further configured to move the end-effector to a location above a collection tray of the one or more collection trays while the at least one gripper of the one or more grippers is holding the produce.

8. The device of claim 7, further comprising:
 a tray cycler coupled to the base, the tray cycler configured to hold the one or more collection trays.

9. A device for harvesting produce from a plant comprising:
 a base;
 an arm coupled to the base; and
 an end-effector coupled to the arm, the end-effector comprising one or more grippers, each of the grippers comprising:
  a first cutter configured to cut a stem of the produce at a first location,
  a second cutter configured to cut the stem of the produce at a second location closer to the produce than the first location,
  a holding member configured to plastically deform to hold the stem of the produce, the holding member disposed between the first cutter and the second cutter,
  one or more collection trays for collecting the produce harvested from the plant, wherein the arm is further configured to move the end-effector to a location above a collection tray of the one or more collection trays while the gripper of the one or more grippers is holding the produce, and
  a tray cycler coupled to the base, the tray cycler configured to hold the one or more collection trays, wherein the tray cycler is further configured to:
   responsive to a first collection tray arranged in a first slot of the tray cycler being full, retract the first collection tray and present a second collection tray arranged in a second slot of the tray cycler;
   move the first collection tray from the first slot of the tray cycler to a third slot of the tray cycler, and
   move a third collection tray from a fourth slot of the tray cycler to the first slot of the tray cycler.

10. The device of claim 1, wherein the first cutter is configured to cut the stem of the produce before the second cutter cuts the stem of the produce, and wherein the holding member is configured to continue to grab onto the stem of the produce after the first cutter cuts the stem of the produce at the first location but before the second cutter cuts the stem of the produce at the second location.

11. The device of claim 1, further comprising:
 a pitch axis actuator for attaching the end-effector to the arm, the pitch axis actuator configured to rotate an angle of the end-effector with respect to the arm.

12. The device of claim 11, wherein the pitch axis actuator is configured to tilt the end-effector while the end-effector is holding the stem of the produce to align a side surface of the produce to a bottom surface of a collection slot for collecting the produce.

13. A gripper for removing plant parts from a plant, comprising:
 a first cutter configured to cut a stem of a produce at a first location,
 a second cutter configured to cut the stem of the produce at a second location closer to the produce than the first location,
 a holding member extending in a first direction, the holding member including a first compliant element and a second compliant element configured to move toward each other in a second direction that intersects the first direction and plastically deform to hold the stem of the produce, the holding member disposed between the first cutter and the second cutter, and
 a first tip and a second tip opposing each other and angled away from distal ends of the compliant members, respectively, the first tip and the second tip configured to guide the stem of the produce in between the first and second compliant members to be accessible by the holding member.

14. The gripper of claim 13, further comprising:
 a first finger and a second finger, the first finger and the second finger coupled to an actuator, the actuator configured to increase or decrease a distance between the first finger and the second finger, wherein the first cutter comprises a first blade attached to the first finger and a second blade attached to the second finger, and the second cutter comprises a third blade attached to the first finger and a fourth blade attached to the second finger.

15. A gripper for removing plant parts from a plant, comprising:
a first cutter configured to cut a stem of a produce at a first location;
a second cutter configured to cut the stem of the produce at a second location closer to the produce than the first location;
a holding member configured to plastically deform to hold the stem of the produce, the holding member disposed between the first cutter and the second cutter; and
a disinfecting module comprising:
one or more tubes configured to deliver one or more chemicals;
one or more nozzles for spraying the one or more chemicals; and
a chemical distributer coupled between the one or more tubes and the one or more nozzles, the chemical distributer configured to control a flow of the one or more chemicals from the one or more tubes to the one or more nozzles.

16. The gripper of claim 14, wherein the first blade of the first cutter is configured to engage with the second blade of the first cutter when the distance between the first finger and the second finger is smaller than a first distance, and wherein the third blade of the second cutter is configured to engage with the fourth blade of the second cutter when the distance between the first finger and the second finger is smaller than a second distance, the second distance smaller than the first distance.

* * * * *